US011600003B2

United States Patent
Sugimoto

(10) Patent No.: US 11,600,003 B2
(45) Date of Patent: Mar. 7, 2023

(54) IMAGE PROCESSING APPARATUS AND CONTROL METHOD FOR AN IMAGE PROCESSING APPARATUS THAT EXTRACT A REGION OF INTEREST BASED ON A CALCULATED CONFIDENCE OF UNIT REGIONS AND A MODIFIED REFERENCE VALUE

(71) Applicant: CANON KABUSHIKI KAISHA, Tokyo (JP)

(72) Inventor: Takashi Sugimoto, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 316 days.

(21) Appl. No.: 17/032,420

(22) Filed: Sep. 25, 2020

(65) Prior Publication Data

US 2021/0090261 A1    Mar. 25, 2021

(30) Foreign Application Priority Data

Sep. 25, 2019   (JP) .............................. JP2019-174320

(51) Int. Cl.
 *G06T 7/11* (2017.01)
 *G06T 7/62* (2017.01)
 (Continued)

(52) U.S. Cl.
 CPC ............ *G06T 7/11* (2017.01); *G06F 3/04842* (2013.01); *G06N 3/04* (2013.01); *G06T 7/50* (2017.01); *G06T 7/62* (2017.01); *G06V 10/25* (2022.01); *G06V 10/50* (2022.01); *G16H 30/20* (2018.01); *G16H 30/40* (2018.01); *G16H 50/20* (2018.01); *G16H 50/30* (2018.01); *G16H 50/50* (2018.01); *G06T 2200/24* (2013.01);
 (Continued)

(58) Field of Classification Search
 None
 See application file for complete search history.

(56) References Cited

U.S. PATENT DOCUMENTS 9,311,570 B2 * 4/2016 Mohr ................. G06K 9/00536
9,756,201 B2 * 9/2017 Kano ................. H04N 1/00244
(Continued)

FOREIGN PATENT DOCUMENTS

JP    2010-097433 A    4/2010
JP    2019-055230 A    4/2019

*Primary Examiner* — Vu Le
*Assistant Examiner* — Courtney Joan Nelson
(74) *Attorney, Agent, or Firm* — Venable LLP

(57) ABSTRACT

An image processing apparatus includes an acquisition unit configured to acquire image data, a calculation unit configured to calculate, for each unit region of the image data, a confidence that the unit region is an extraction subject, the confidence as the extraction subject being calculated for each unit region of the image data by inputting the image data into a trained model of a neural network that has been trained using images of an existing extraction subject or a region of interest as training data, a modification unit configured to modify a reference value of the confidence, which is used to extract a region of interest, an extraction unit configured to extract the region of interest on the basis of the calculated confidence of each unit region and the modified reference value, and a display unit configured to display the extracted region of interest.

15 Claims, 17 Drawing Sheets

(51) Int. Cl.
*G06T 7/50* (2017.01)
*G16H 30/20* (2018.01)
*G16H 30/40* (2018.01)
*G16H 50/50* (2018.01)
*G16H 50/30* (2018.01)
*G16H 50/20* (2018.01)
*G06N 3/04* (2006.01)
*G06F 3/04842* (2022.01)
*G06V 10/50* (2022.01)
*G06V 10/25* (2022.01)

(52) U.S. Cl.
CPC ............... *G06T 2207/20081* (2013.01); *G06T 2207/20084* (2013.01); *G06T 2207/20104* (2013.01); *G06T 2207/30088* (2013.01); *G06V 2201/03* (2022.01)

(56) References Cited

U.S. PATENT DOCUMENTS

| | | | | |
|---|---|---|---|---|
| 2006/0274928 A1* | 12/2006 | Collins | ................... | G16H 30/40 |
| | | | | 382/132 |
| 2008/0205717 A1* | 8/2008 | Reeves | ................... | G06T 5/002 |
| | | | | 382/128 |
| 2012/0189176 A1* | 7/2012 | Giger | ................... | G06T 19/20 |
| | | | | 382/128 |
| 2018/0182101 A1* | 6/2018 | Petersen | ................... | G06T 7/11 |

* cited by examiner

IMAGE PROCESSING APPARATUS AND CONTROL METHOD FOR AN IMAGE PROCESSING APPARATUS THAT EXTRACT A REGION OF INTEREST BASED ON A CALCULATED CONFIDENCE OF UNIT REGIONS AND A MODIFIED REFERENCE VALUE

CROSS-REFERENCE TO PRIORITY APPLICATION

This application claims the benefit of Japanese Patent Application No. 2019-174320, filed on Sep. 25, 2019, which is hereby incorporated by reference herein in its entirety.

BACKGROUND OF THE INVENTION

Field of the Invention

The present invention relates to an image processing apparatus that extracts a region of a subject on the basis of an image of the subject, and a control method for the image processing apparatus.

Description of the Related Art

Patients who develop pressure ulcers in medical care settings and nursing care settings require periodical assessments of the pressure ulcers, and measuring the size of a pressure ulcer is one index for ascertaining the progression of the pressure ulcer. A pressure ulcer state determination scale "DESIGN-R"®, developed by the Scientific Education Committee of the Japanese Society of Pressure Ulcers, has been proposed as a tool for assessing a pressure ulcer. "DESIGN-R" is a tool for assessing the healing process of pressure ulcers and other wounds. The name of the tool is taken from the respective first letters of the following assessment indices, namely Depth, Exudate, Size, Inflammation/Infection, Granulation, and Necrotic tissue. "DESIGN-R" uses scores to assess the healing process of the pressure ulcer and select appropriate care, and it is indicated that scoring is performed periodically in order to assess and manage the pathological condition.

The "size" assessment of "DESIGN-R" is used to measure (in cm units) the major axis and the minor axis (the maximum diameter perpendicular to the major axis) of a skin damage range and classify the size into one of seven levels from a numerical value acquired by multiplying the measured values.

In the affected-area region of a pressure ulcer, the acquired size varies depending on the two points used as the points between which the major and minor axes are measured. Therefore, in order to assess the healing process, and so on, of the pressure ulcer correctly, a healthcare worker must appropriately adjust the way of applying a measure or the like to the affected-area region of the pressure ulcer each time.

With regard to automatic recognition of a region, Japanese Patent Application Publication No. 2010-97433 discloses a technique for capturing an image including wires, electrodes, and the like, of a substrate and recognizing a region automatically on the basis of a selected color gamut. Japanese Patent Application Publication No. 2019-55230 discloses a technique for correcting an automatically recognized region on the basis of another structure region.

When a specific region such as a wound formed on the surface layer of a subject is automatically recognized by image processing, the following problem may occur. When the affected-area region of a pressure ulcer, or the like, as described above, is used as an example of the specific region, an imaging apparatus determines the extent of the affected area during imaging. However, the range of the image of the affected area required to perform an assessment often differs according to the aim of the assessment carried out by the healthcare worker.

For example, the healthcare worker may assess only the range of the affected area in which the damage is greatest or may assess a wide range extending from the center of the affected area to an area of normal skin on the outer edge.

Further, when the affected-area region is extracted using a classifier acquired using a machine learning method such as deep learning and the amount of training data used for learning is insufficient or the data are inaccurate, the determination made by the healthcare worker may differ from the determination made by the imaging apparatus. With the technique disclosed in Japanese Patent Application Publication No. 2010-97433, when an affected-area region that differs from the determination of the user is extracted, the user can re-extract the affected-area region by reselecting the color gamut used to extract the affected-area region. However, it is difficult to re-extract the affected-area region so as to exclude regions that have the same color gamut as the affected-area region but are not the affected-area region.

With the technique disclosed in Japanese Patent Application Publication No. 2019-55230, the affected-area region is corrected on the basis of a structure region other than the affected-area region, but when there are no structures that can be referred to in order to correct the affected-area region on the periphery of the affected-area region, the affected-area region is not corrected. Moreover, due to the absence of correcting means that interact with the user, it is difficult to make fine adjustments to the region.

The present invention has been designed in consideration of the problems described above, and an object thereof is to allow a user to adjust a region of interest extracted from an image of a subject while visually checking the region of interest.

SUMMARY OF THE INVENTION

An image processing apparatus of the present invention includes an acquisition unit configured to acquire image data, a calculation unit configured to calculate, for each unit region of the image data, a confidence that the unit region is an extraction subject, the confidence as the extraction subject being calculated for each unit region of the image data by inputting the image data into a trained model of a neural network that has been trained using images of an existing extraction subject or a region of interest as training data, a modification unit configured to modify a reference value of the confidence, which is used to extract a region of interest, an extraction unit configured to extract the region of interest on the basis of the calculated confidence of each unit region and the modified reference value, and a display unit configured to display the extracted region of interest.

Further features of the present invention will become apparent from the following description of exemplary embodiments with reference to the attached drawings.

DESCRIPTION OF THE EMBODIMENTS

Preferred embodiments of the present invention will be described below with reference to the figures.

First Embodiment

Figure 1:
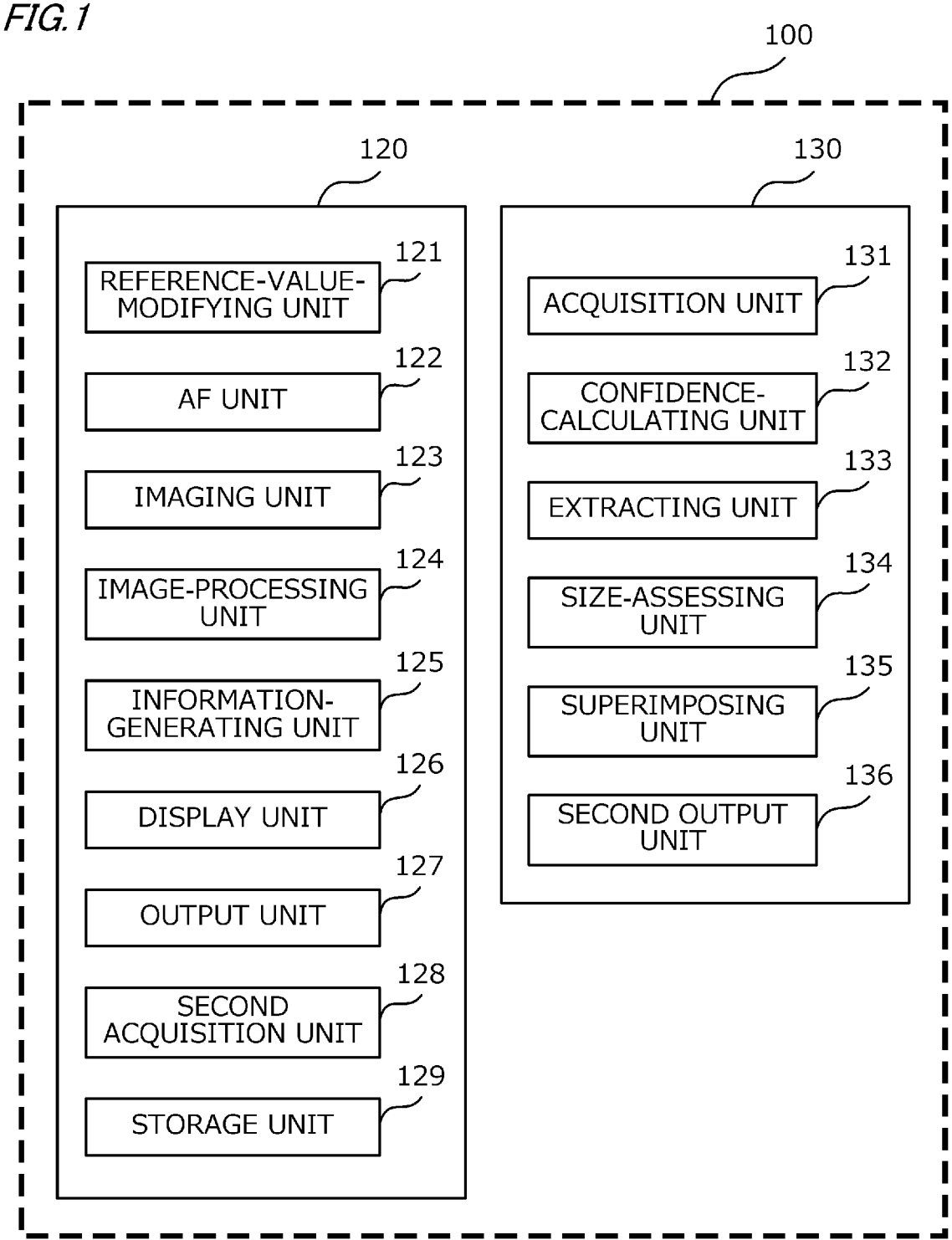
FIG. 1 is a view showing an example functional configuration of an image processing system of a first embodiment.
Figure 2:
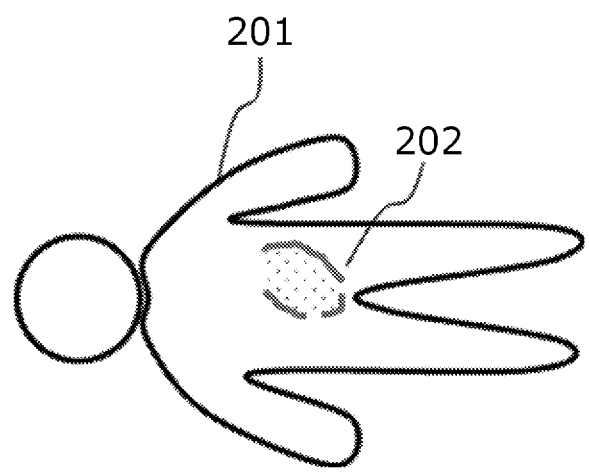
FIG. 2 is a view showing an example of a subject.

First, referring to FIGS. 1 to 4, an image processing system according to a first embodiment will be described. FIG. 1 is a view showing an example functional configuration of the image processing system according to the first embodiment. An image processing system 100 includes an imaging apparatus 120 and an image processing apparatus 130. FIG. 2 is a view showing an example of a subject to be measured by the image processing system 100. In this embodiment, a pressure ulcer will be described as an example of a pathological condition of an affected-area region 202 formed on the buttocks of a subject 201.

The image processing system 100 captures an image including the affected-area region 202 of the subject 201, and acquires the distance to the subject. The image processing system 100 calculates, for each pixel of the captured image data, a confidence that the relevant pixel will be classified as a pressure ulcer serving as an extraction subject (the confidence as a pressure ulcer). Here, the pixel corresponds to a unit region of the image data.

Here, the confidence will be described. The confidence is a numerical value expressing a classification probability. Examples of machine learning algorithms for classifying images by calculating confidence values include an SVM (Support Vector Machine) and deep learning. A multiclass classifier of an SVM calculates the probability that an input image will be classified into respective classification candidate classes on the basis of a distance between a feature vector of the input image and a separation hyperplane of the classifier. The classifier outputs the calculated value as a confidence. An identifier classifies the input image into the class for which the confidence is highest. The classification candidate classes correspond to the extraction subject and will also be referred to hereafter as a classification class.

Deep learning, meanwhile, includes tasks such as classification and semantic region segmentation. In the classification task performed during deep learning, when an image to be classified is input into a neural network, a feature of the image is extracted in an intermediate layer of the neural network, and the probability of classification into each of the classification classes can be calculated in an output layer. Further, the image processing system 100 outputs, as the confidence, a value acquired by normalizing the calculated probability of classification into each class to a range of real numbers of at least 0 and not more than 1 using a softmax function so that the sum of all classes equals 1. As a result, the calculated confidence values can be interpreted as the probabilities of being classified into the respective classes. The image processing system 100 then classifies the image into the class for which the confidence is highest.

Further, in the semantic region segmentation task performed during deep learning, the image processing system 100 calculates a confidence for each pixel of the input image instead of calculating a confidence for the input image as a whole. More specifically, in the semantic region segmentation performed during deep learning, the output layer outputs a confidence map of a size corresponding to (number of pixels of input image)×(number of classification classes). These confidence values express the confidence with which the respective pixels of the input image are classified into the classification classes. Similarly to the classification task, the confidence calculated for each pixel is normalized to a range of real numbers of at least 0 and not more than 1 using a softmax function. As a result, the confidence of each pixel can be interpreted as the probability that the pixel will be classified into each class. By classifying each pixel into the class in which the confidence is highest, the image processing system 100 can divide a region among the classes.

In the example described in this embodiment, the confidence as a pressure ulcer is calculated for each pixel of an image using the semantic region segmentation task performed during deep learning. The image processing system 100 extracts, or performs region segmentation on, the affected-area region 202 on the basis of the calculated confidence of each pixel. In the following description, the affected-area region 202 is an extraction result extracted, or subjected to region segmentation, by the image processing system 100, and the affected-area region 202 corresponds to a region of interest.

The image processing system 100 displays the extraction result (the region segmentation result) acquired in relation to the affected-area region 202 using display means of the imaging apparatus 120. A user confirms whether the displayed region segmentation result is too large or too small. When the result is too large or too small, the user performs an operation to set a reference value of the confidence values of the respective pixels, or, in other words, a reference value for extracting a region having a confidence with at least a specific numerical value. The image processing system 100 then extracts, or performs region segmentation on, the affected-area region 202 again on the basis of the set confidence reference value and the confidence values of the respective pixels.

For example, when the user sets the confidence reference value at 90, the user may wish to include a slightly wider range than that of the extracted affected-area region 202 as the pressure ulcer. In this case, the user can make an adjustment by lowering the confidence to 85 or 80 so that the affected-area region 202 is extracted in the desired range. The user makes repeated adjustments interactively while visually checking the image until s/he determines that the appropriate affected-area region 202 has been extracted, and, in so doing, an appropriately corrected region segmentation result can be acquired.

The image processing system 100 measures a surface area per pixel on the basis of the distance to the subject and the angle of view of a camera. The image processing system 100 can calculate the surface area of the affected-area region 202 from the adjusted region and the surface area per pixel. Note that the extraction subject is not limited to a pressure ulcer and may be a burn, a laceration, and so on. The extraction subject is not limited to the affected area and may be any object on an image in the form of electronic data. Note that, when the pathological condition of the subject affected area changes, a different semantic region is used during deep learning, and, therefore, when the pathological condition of the subject affected area changes, a system corresponding to the pathological condition is used.

Functional Configuration of Imaging Apparatus A functional configuration of the imaging apparatus 120 shown in FIG. 1 will now be described. For example, the imaging apparatus 120 is a portable device that can be hand-held by the user. The imaging apparatus 120 includes reference-value-modifying unit 121, AF unit 122 (Auto Focus unit), imaging unit 123, image-processing unit 124, information-generating unit 125, display unit 126, output unit 127, second acquisition unit 128, and storage unit 129. Note that the imaging apparatus 120 is not limited to a digital still camera or a digital movie camera and may also be a mobile telephone, a tablet, or the like, for example. Further, the imaging apparatus 120 is preferably a portable device that can be hand-held by the user but is not limited thereto. The imaging apparatus 120 may also be a medical camera, or the like.

The reference-value-modifying unit 121 modifies the confidence reference value used to extract the affected-area region 202. The reference-value-modifying unit 121 can modify the confidence reference value on the basis of a user operation, for example. Note that the reference-value-modifying unit 121 may be provided in the image processing apparatus 130 instead of being included in the imaging apparatus 120.

The AF unit 122 has an automatic focus adjustment function for automatically focusing on the subject 201. Further, the AF unit 122 outputs the distance (the subject distance) to the subject 201 from a focus adjustment amount or a movement amount of a focus lens.

The imaging unit 123 generates image data by photographing the subject 201. The image-processing unit 124 resizes the image acquired by the imaging unit 123 by performing image processing, including development, on the image.

The information-generating unit 125 generates distance information relating to the distance to the subject 201. For example, the information-generating unit 125 may generate the distance information on the basis of the subject distance output by the AF unit 122.

The display unit 126 performs various types of display control. The display unit 126 performs display based on at least one of the image captured by the imaging unit 123, information indicating the affected-area region 202, information relating to the size of the affected-area region 202, and information relating to the confidence reference value used to extract the affected-area region 202. The display unit 126 may display at least one of the types of information described above so as to be superimposed on the image captured by the imaging unit 123.

The output unit 127 outputs the image data, the distance information relating to the distance to the subject 201, and information relating to the confidence reference value set by the reference-value-modifying unit 121 to the image processing apparatus 130 or an external apparatus.

The second acquisition unit 128 acquires the following information from either an external apparatus or the image processing apparatus 130. Specifically, the second acquisition unit 128 acquires the image data generated by the image processing apparatus 130, information indicating the extracted affected-area region, and information relating to the size of the affected-area region 202.

Functional Configuration of Image Processing Apparatus Next, a functional configuration of the image processing apparatus 130 shown in FIG. 1 will be described. The image processing apparatus 130 is an example of an external apparatus relating to the imaging apparatus 120, and includes acquisition unit 131, confidence-calculating unit 132, extracting unit 133, size-assessing unit 134, superimposing unit 135, and second output unit 136.

The acquisition unit 131 acquires the image data, the distance information relating to the distance to the subject 201, and the information relating to the confidence reference value set by the reference-value-modifying unit 121, output by the imaging apparatus 120. From the image data, the confidence-calculating unit 132 calculates the confidence as a pressure ulcer for each pixel of the image data.

The extracting unit 133 extracts the affected-area region 202 on the basis of the confidence calculated for each pixel of the image data by the confidence-calculating unit 132 and the confidence reference value acquired by the acquisition unit 131. Here, extracting a region from the image data is also known as region segmentation.

The size-assessing unit 134 calculates an assessment value of the size of the affected-area region 202 extracted by the extracting unit 133 on the basis of the distance information relating to the distance to the subject 201, acquired by the acquisition unit 131.

The superimposing unit 135 superimposes information indicating the extracted affected-area region 202, information relating to the size of the affected-area region 202, and information relating to the confidence reference value used to extract the affected-area region on the image data used to extract the affected-area region 202.

The second output unit 136 outputs image data generated by the superimposing unit 135, information relating to the affected-area region extracted by the extracting unit 133, and information relating to the size of the affected-area region 202, calculated by the size-assessing unit 134.

Figure 3:
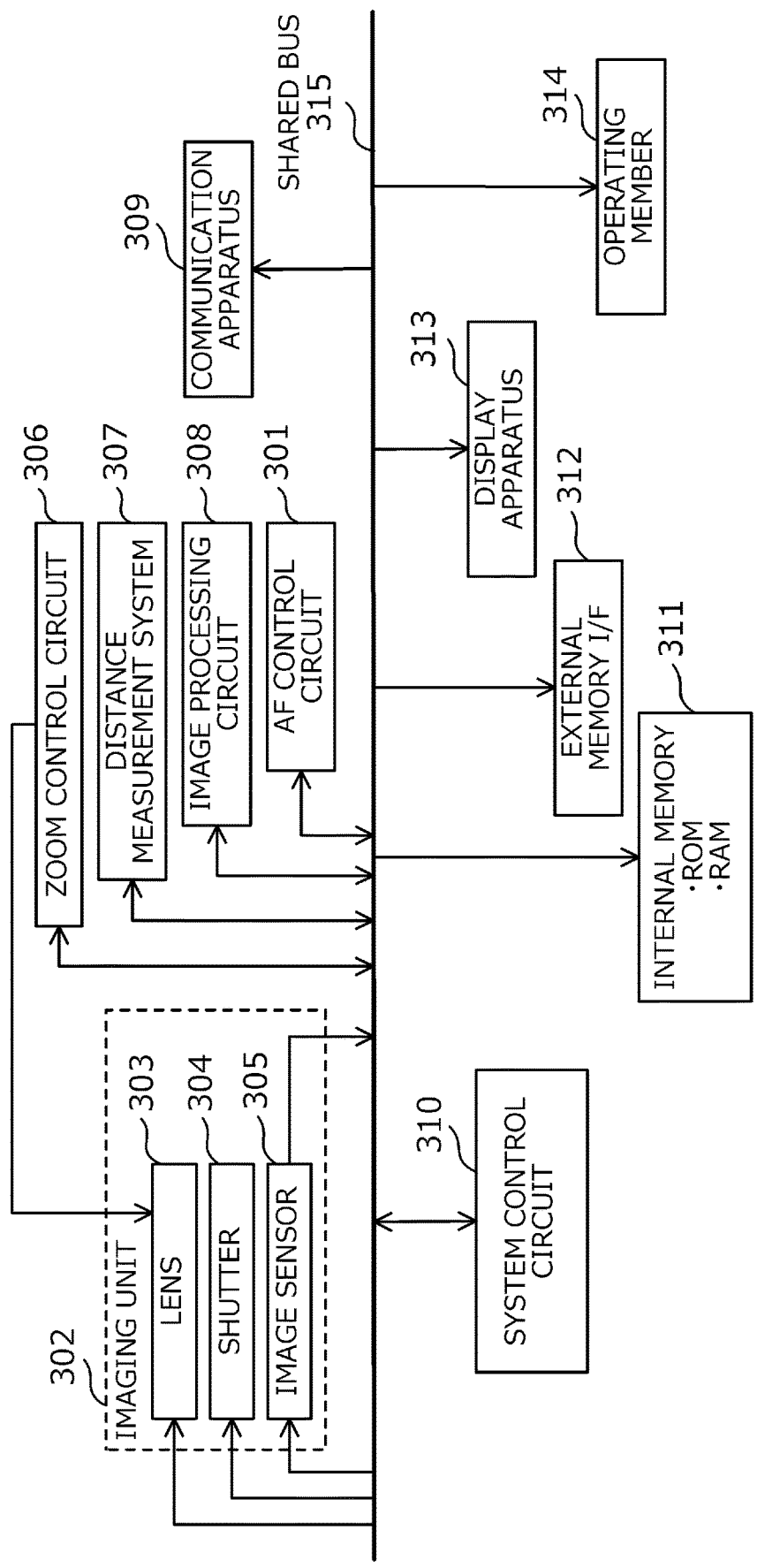
FIG. 3 is a view showing an example hardware configuration of an imaging apparatus.

Hardware Configuration of Imaging Apparatus Referring to FIG. 3, a hardware configuration of the imaging apparatus 120 will be described. FIG. 3 is a view showing an example hardware configuration of the imaging apparatus 120. The imaging apparatus 120 includes an AF control circuit 301, an imaging unit 302, a zoom control circuit 306, a distance measurement system 307, an image processing circuit 308, a communication apparatus 309, and a system control circuit 310. The imaging apparatus 120 further includes an internal memory 311, an external memory I/F (Interface) 312, a display apparatus 313, an operating member 314, and a shared bus 315.

The AF control circuit 301 adjusts the focus automatically by extracting a high-frequency component of an imaging signal (a video signal), searching for a focus lens position in which the extracted high-frequency component reaches a maximum, and controlling the focus lens. The focus lens is included in a lens 303. This focus control method is known as TV-AF or contrast AF, and a feature thereof is that high-precision focusing can be realized. Further, the AF control circuit 301 outputs the distance to the subject 201 on the basis of the focus adjustment amount or the movement amount of the focus lens.

The focus control method is not limited to contrast AF, and phase difference AF or another AF method may be used instead. Furthermore, the AF control circuit 301 can detect the focus adjustment amount or the position of the focus lens and acquire the distance to the subject 201 on the basis of the position of the focus lens. The AF unit 122 of the imaging apparatus 120 is realized by operating the AF control circuit 301.

The imaging unit 302 includes the lens 303, a shutter 304, and an image sensor 305. The imaging unit 123 of the imaging apparatus 120 is realized by operating the imaging unit 302.

The lens 303 forms an optical image of the subject 201 on the image sensor 305. The lens 303 includes an aperture that determines an aperture value used to adjust the exposure amount. The image sensor 305 includes a charge storage-type solid state image sensor such as a CCD or a CMOS element that converts optical images into electrical signals.

The shutter 304 controls the shutter speed by opening and closing so as to expose and to shield the image sensor 305. Note that the shutter 304 is not limited to a mechanical shutter, and an electronic shutter may be used instead. In an imaging element that uses a CMOS sensor, the electronic shutter first performs a reset scan on each pixel or each region of a plurality of pixels (for example, each line) in order to set the amount of charge stored in the pixel at zero. Next, after a predetermined time elapses in each pixel or each region of a plurality of pixels following implementation of the reset scan, the imaging unit 302 performs a scan to read a signal therefrom.

The zoom control circuit 306 controls driving of a zoom lens included in the lens 303. The zoom control circuit 306 drives the zoom lens using a zoom motor (not shown) in response to an instruction from 310. As a result, scaling is performed.

The distance measurement system 307 has functions for dividing an image surface into predetermined blocks constituted by pluralities of pixels and detecting the distance to the subject 201 in each block on the image surface. The distance measurement system 307 thus serves as a unit for detecting the distance to the subject 201. The distance measurement system 307 may also detect the distance to the subject 201 on the basis of the output of the AF control circuit 301. When a plurality of blocks exist on the image surface, the distance measurement system 307 detects the distance to the subject 201 in each block by performing the AF operation repeatedly on each block.

Note that a system using a TOF (Time of Flight) sensor may be used as an example of the distance measurement system 307. A TOF sensor is a sensor that measures the distance to an object on the basis of a time difference (or a phase difference) between the transmission timing of an irradiation wave and the reception timing of a reflected wave generated when the irradiation wave is reflected by the object. A system using a PSD method, in which a PSD (Position Sensitive Device) is used as a reception element, or the like, may also be used as the distance measurement system 307. The information-generating unit 125 generates the distance detected by the distance measurement system 307 as the distance information.

The image processing circuit 308 implements image processing on RAW image data output from the image sensor 305. The image processing circuit 308 performs various types of image processing on the image data (RAW image data) output from the imaging unit 302 or image signal data stored in the internal memory 311, to be described below. The image processing includes at least one of white balance adjustment, gamma correction, color interpolation, demosaicing, and filtering, for example. Further, the image processing circuit 308 performs compression processing on the data of the image signal captured by the imaging unit 302 according to JPEG standards, or the like.

The communication apparatus 309 is a communication interface by which the respective configurations in the imaging apparatus 120 communicate with an external apparatus such as the image processing apparatus 130 over a wireless network (not shown). The output unit 127 and the second acquisition unit 128 are realized by operating the communication apparatus 309. A network based on Wi-Fi® standards may be cited as a specific example of the network. Note that Wi-Fi communication may be realized through a router. The communication apparatus 309 may also be realized by a wired communication interface such as a USB or a LAN.

The system control circuit 310 includes a CPU (Central Processing Unit). The system control circuit 310 performs overall control by controlling the respective parts of the imaging apparatus 120 in accordance with a program stored in the internal memory 311. The system control circuit 310 also performs overall control of the AF control circuit 301, the imaging unit 302, the zoom control circuit 306, the distance measurement system 307, the image processing circuit 308, and so on.

The internal memory 311 includes a nonvolatile memory such as a ROM, in which programs are recorded, and a system memory such as a RAM, which is used by the system control circuit 310 as a working memory for work. The internal memory 311 temporarily stores various setting information, such as information about the focus position at the time of image capture, which is required in the operation of the imaging apparatus 120, the image captured by the imaging unit 302, and the image acquired as a result of the processing performed by the image processing circuit 308. The internal memory 311 may also temporarily store image data, analysis data such as information relating to the size of the affected-area region 202, the confidence reference value used to extract the affected-area region 202, and so on, all of which are received by the communication apparatus 309 through communication with the image processing apparatus 130. The internal memory 311 is constituted by a nonvolatile, rewritable memory such as a flash memory, an SDRAM, or the like, for example.

The external memory I/F 312 is an interface with a nonvolatile storage medium that can be attached to the main body of the imaging apparatus 120 or a nonvolatile storage medium fixed to the interior of the imaging apparatus 120. The external memory is an SD card, a CF card, or the like, for example. The external memory I/F 312 stores the image data processed by the image processing circuit 308 and the image data, analysis data, and so on, received by the communication apparatus 309 through communication with the image processing apparatus 130 in the storage medium that can be attached to the main body of the imaging apparatus 120. Further, when the image data are to be reproduced, the external memory I/F 312 reads the image data stored in the storage medium that can be attached to the main body of the imaging apparatus 120. The external memory I/F 312 can display the read image data on the display apparatus 313 or output the image data to the outside of the imaging apparatus 120.

The display apparatus 313 displays the image stored temporarily in the internal memory 311, the image and data stored in the external memory I/F 312, a setting screen of the imaging apparatus 120, and so on. The display apparatus 313 is constituted by, for example, a TFT (Thin Film Transistor) liquid crystal display, an organic EL display, an EVF (Electronic Viewfinder), or the like. The display unit 126 corresponds to the display apparatus 313.

The operating member 314 is constituted by, for example, buttons, switches, keys, and a mode dial provided on the imaging apparatus 120. Alternatively, for example, the imaging apparatus 120 is formed integrally with the display apparatus 313 and includes a touch panel capable of detecting contact with a display surface. User commands such as a mode setting, an imaging operation such as a release operation, and a setting for the confidence reference value to be used to extract the affected-area region 202 are transmitted to the system control circuit 310 through the operating member 314.

The AF control circuit 301, the imaging unit 302, the zoom control circuit 306, the distance measurement system 307, and the image processing circuit 308 are connected to the shared bus 315. The communication apparatus 309, the system control circuit 310, the internal memory 311, the external memory I/F 312, the display apparatus 313, and the operating member 314 are also connected to the shared bus 315. The shared bus 315 is a signal line for transmitting and receiving signals to and from the respective blocks.

Note that the imaging apparatus 120 may be formed using a lens unit that can be attached to and detached from the imaging apparatus main body and includes an imaging element. In this case, the imaging apparatus main body does not include an imaging element.

Hardware Configuration of Image Processing Apparatus

Figure 4:
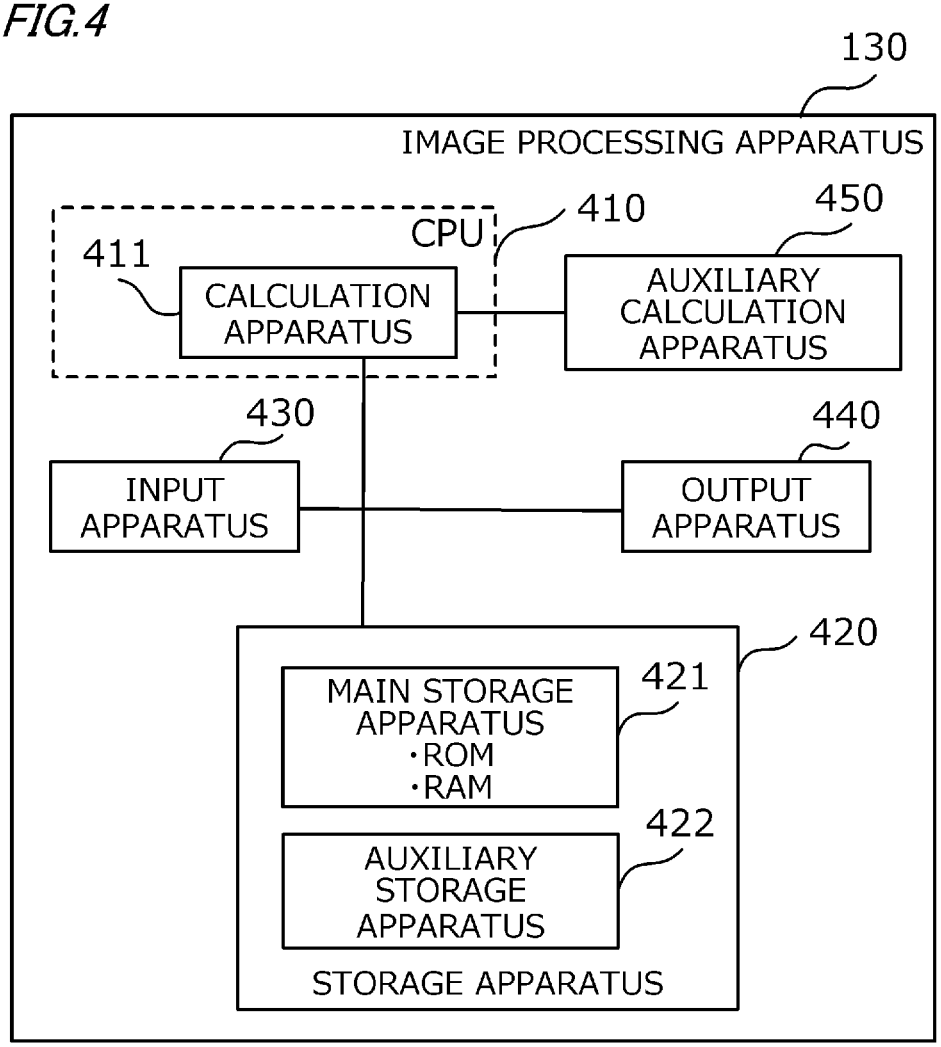
FIG. 4 is a view showing an example hardware configuration of an image processing apparatus of the first embodiment.

Next, referring to FIG. 4, a hardware configuration of the image processing apparatus 130 will be described. FIG. 4 is a view showing an example hardware configuration of the image processing apparatus 130. In the example of FIG. 4, the image processing apparatus 130 includes a central calculation processing apparatus 410, a storage apparatus 420, an input apparatus 430, an output apparatus 440, and an auxiliary calculation apparatus 450. Hereafter, the central calculation processing apparatus 410 will be referred to as the CPU 410.

The CPU 410 includes a calculation apparatus 411. The storage apparatus 420 includes a main storage apparatus 421 and an auxiliary storage apparatus 422. The main storage apparatus 421 includes a nonvolatile memory such as a ROM, in which programs are recorded, and a system memory such as a RAM, which is used by the CPU 410 as a working memory for work. The auxiliary storage apparatus 422 is a magnetic disk apparatus, an SSD (Solid State Drive), or the like, for example.

The input apparatus 430 is a mouse, a keyboard, or the like, for example. Note that the image processing apparatus 130 may include, as the input apparatus 430, a touch panel display, or the like, in which a touch panel is formed integrally with the output apparatus 440. The output apparatus 440 is a computer display, for example. The input apparatus 430 and the output apparatus 440 may be partially formed as a wireless communication module that communicates using Wi-Fi.

The auxiliary calculation apparatus 450 is an auxiliary calculation IC used under the control of the CPU 410. A GPU (Graphic Processing Unit), for example, can be used as the auxiliary calculation apparatus 450. A GPU is originally a processor used for image processing, but a GPU includes a plurality of multiplier-accumulators and is good at matrix calculation and is, therefore, also used as a processor for performing signal learning processing. A GPU is also typically used in deep learning processing. Note that an FPGA (Field-Programmable Gate Array), an ASIC, or the like, may also be used as the auxiliary calculation apparatus 450.

By executing a program stored in the storage apparatus 420, the calculation apparatus 411 functions as the acquisition unit 131, the confidence-calculating unit 132, the extracting unit 133, the size-assessing unit 134, the superimposing unit 135, and the second output unit 136 of the image processing apparatus 130. Further, the calculation apparatus 411 controls the order in which the acquisition unit 131, the confidence-calculating unit 132, the extracting unit 133, the size-assessing unit 134, the superimposing unit 135, and the second output unit 136 are executed.

Note that the CPU 410 and the storage apparatus 420 of the image processing apparatus 130 may be provided either singly or in a plurality. In other words, at least one processing apparatus (CPU) and at least one storage apparatus are connected so that when the at least one processing apparatus executes a program stored in the at least one storage apparatus, the image processing apparatus 130 functions as the units listed above. Note that the processing apparatus is not limited to a CPU and may be an FPGA, an ASIC, or the like.

Operation of Image Processing System

Figure 5:
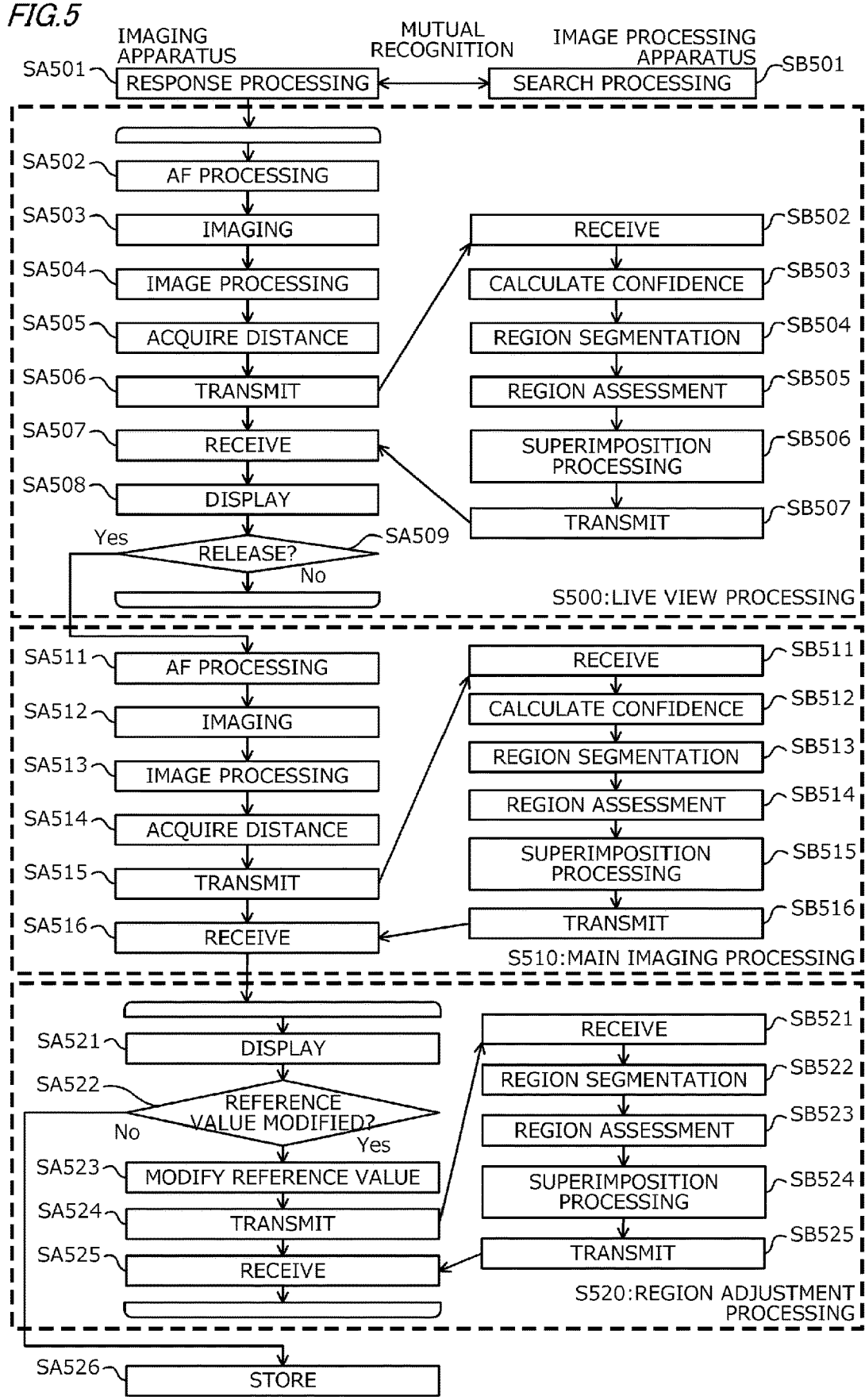
FIG. 5 is a view illustrating an example operation of the image processing system of the first embodiment.

Referring to FIG. 5, an operation of the image processing system according to this embodiment will be described. FIG. 5 is a view illustrating an example operation (an example of processing executed according to a flowchart) of the image processing system 100 according to the first embodiment.

Hereafter, on the flowcharts describing operations of the image processing system 100, processing executed by the imaging apparatus 120 will be indicated by reference numerals starting with "SA", while processing executed by the image processing apparatus 130 will be indicated by reference numerals starting with "SB". The processing executed by the imaging apparatus 120 is realized by having the system control circuit 310 expand a program stored in the nonvolatile internal memory 311 in the system memory and execute the program. The processing executed by the image processing apparatus 130 is realized by having the CPU 410 expand a program stored in the ROM of the main storage apparatus 421 in the system memory (the RAM) and execute the program. Note that the processing of FIG. 5 is started when power is supplied to the imaging apparatus 120 and the imaging apparatus 120 responds to search processing executed by the image processing apparatus 130.

In response processing of SA501 and search processing of SB501, the imaging apparatus 120 and the image processing apparatus 130 are respectively connected to a WiFi standard network (not shown), for example, the WiFi standard being a wireless LAN standard, so as to recognize each other. In SB501, the image processing apparatus 130 searches for the imaging apparatus 120 connected to the image processing apparatus 130. In SA501, the imaging apparatus 120 responds to the search processing executed by the image processing apparatus 130. The search is performed by the image processing apparatus 130 using any of various device search techniques executed through a network. UPnP (Universal Plug and Play), for example, is a device search technique. In UPnP, individual apparatuses are recognized by UUIDs (Universally Unique Identifiers). Note that the communication format is not limited to an infrastructure mode in which the respective apparatuses communicate via an access point of a wireless LAN, and the imaging apparatus 120 and image processing apparatus 130 may communicate by P2P (Peer to Peer) communication using an ad-hoc mode.

S500: Live View Processing

Next, live view processing S500 will be described. The live view processing S500 is processing for displaying a live video on the display apparatus 313 (the display unit 126) of the imaging apparatus 120. The live view processing S500 includes processing of SA502 to SA509, executed by the imaging apparatus 120, and processing of SB502 to SB507, executed by the image processing apparatus 130.

In SA502, the AF unit 122 performs AF processing. In the AF processing, the focus is automatically adjusted in order to focus on the affected-area region 202. The AF unit 122 divides the image surface into a plurality of blocks and performs AF (Auto Focus) on a predetermined block. In this embodiment, it is assumed that the imaging apparatus 120 is held so that the affected-area region 202 is located in the center of the image surface. Accordingly, the AF unit 122 performs AF on the block positioned in the center of the image surface. Further, the AF unit 122 outputs the distance to the AF area of the subject 201 from the focus adjustment amount or the movement amount of the focus lens.

In SA503, the imaging unit 123 captures an image of the subject 201 so as to include the affected-area region 202 of the subject 201. Note that following SA501, the processing from SA502 to SA509 is repeated until a release instruction is issued in SA509.

In SA504, the image-processing unit 124 develops the image captured in SA503 and performs image compression on the developed image using a standard such as JPEG. The image-processing unit 124 then resizes the acquired image. The image generated in SA504 is transmitted to the image processing apparatus 130 in SA506, to be described below, by wireless communication.

Here, image resizing will be described. The larger the image transmitted to the image processing apparatus 130, the longer it takes to transmit the image by wireless communication. Therefore, the size of the image following resizing is selected in consideration of the communication time allowed between the imaging apparatus 120 and the image processing apparatus 130.

Further, in SB504, to be described below, processing for calculating the confidence as a pressure ulcer is performed on each pixel of the image. The time required for the calculation processing and the calculation precision depend on the image size. Therefore, the size of the image following resizing is selected also in consideration of these requirements.

Furthermore, the processing of SA504 is performed during the live view processing, and, therefore, when the processing time is long, the frame rate of the live video may decrease. In the live view processing S500, the image-processing unit 124 can suppress a reduction in the frame rate by resizing the image to or below the size to which the image is resized during image processing in main imaging processing (SA513 of S510, to be described below). For example, in SA504, the image-processing unit 124 can resize the image to a size of approximately 1.1 megabytes with 720 pixels×540 pixels and 8-bit RGB color, for example. The size of the resized image is not limited thereto, and any size allowing live view display at a predetermined frame rate may be used.

In SA505, the information-generating unit 125 generates distance information relating to the distance to the subject 201. More specifically, the information-generating unit 125 generates the distance information on the basis of the distance to the AF area of the subject 201, acquired in the AF processing of SA502. Further, when the AF processing is performed on each of the plurality of blocks acquired by dividing the image surface in SA502, the information-generating unit 125 may acquire the distance to the subject 201 for each of the plurality of blocks. Note that the information-generating unit 125 may generate the distance information using a TOF (Time Of Flight) sensor or the like, or another sensor.

In SA506, the output unit 127 transmits (outputs) the image data generated in SA504 and the distance information relating to the distance to the subject 201, generated in SA505, to the image processing apparatus 130.

The image processing apparatus 130 executes the processing from SB502 to SB507. In SB502, the acquisition unit 131 receives (acquires) the image data and the distance information relating to the distance to the captured subject 201, output from the imaging apparatus 120.

In SB503, the confidence-calculating unit 132 calculates the confidence as a pressure ulcer for each pixel of the image data acquired in SB502. In this case, the confidence-calculating unit 132 does not have to calculate confidence values for the entire region of the image data. The clothing worn by the patient, the hand of the photographer, and so on, for example, may appear on the captured image, and, therefore, the confidence-calculating unit 132 may be configured to calculate confidence values within a range specified by the user.

Semantic region segmentation performed during deep learning may be cited as an example of a method for calculating the confidence of each pixel. In semantic region segmentation, a training computer (not shown) generates a trained model by training a model of a neural network using a plurality of images of affected areas of actual pressure ulcers, in which the affected-area region is known, as training data. The confidence-calculating unit 132 calculates the confidence that each pixel of the input image is a pressure ulcer on the basis of the generated trained model.

The calculated confidence is not limited to the confidence as a pressure ulcer. The confidence-calculating unit 132 may, for example, calculate the confidence of being classified as a region of normal skin (the confidence as a region of normal skin) or the confidence of being classified as a background region other than the skin (the confidence as a background region). "Pressure ulcer", "normal skin region", and "background region", into which the pixels are respectively classified, are examples of classification classes.

In this embodiment, a Fully Convolutional Network (FCN), which is a segmentation model using deep learning, is applied as an example of the model of the neural network. In an FCN, the confidence with which each pixel is classified into each of the classification classes is output so that the sum of the confidence values calculated for the respective classes is 1.

An example of the calculation content of an FCN network will be described below. First, in a convolution layer, a convolution calculation is performed on the input image, whereupon a value is output through an activation function. In a pooling layer, a pooling operation is performed to extract a representative value from a plurality of pixels. Down-sampling is then performed by calculations using a plurality of combinations so as to allow overlap between the convolutional layer and the pooling layer, whereby a three-dimensional feature map is acquired. Next, features corresponding to (number of pixels in input image)×(number of classification classes) are acquired in relation to the acquired three-dimensional feature map by calculating, a plurality of times, the sum of a feature map acquired after up-sampling the acquired three-dimensional feature map using a deconvolution layer and a feature map prior to the down-sampling. These features represent scores indicating whether or not the pixels of the input image will be classified into the classification classes. The scores indicating whether or not the pixels will be classified into the classification classes are then normalized to a range of real numbers of at least 0 and not more than 1 using a softmax function so that the sum of all classes equals 1. The FCN then outputs these values as the confidence that each of the pixels will be classified into the respective classification classes.

Here, the inference of the deep learning is processed by the GPU included in the auxiliary calculation apparatus 450, which is good at executing product-sum operations in parallel. The inference processing may also be executed by an FPGA, an ASIC, or the like. Further, the confidence of each pixel may be calculated using another deep learning model. Note that the confidence calculation method is not limited to deep learning. For example, with respect to a certain focus pixel, a feature such as a SIFT (Scale-Invariant Feature Transform) feature is extracted from a region on the periphery of the focus pixel (a rectangular region centering on the focus pixel, for example). The extracted feature may then be input into an identifier such as an SVM, and the value of the output thereof may be calculated as the confidence of the focus pixel. Note that the confidence calculation is not limited to being executed only in pixel units. For example, the input image may be partitioned into rectangular cell units including m pixels vertically and n pixels horizontally (where m and n are arbitrary natural numbers), and the confidence may be calculated for each cell. Furthermore, the partitioned shape is not limited to rectangular cells, and segments of any desired shape may be used.

In SB504, the extracting unit 133 extracts, or performs region segmentation on, the affected-area region 202 of the subject 201 from the image data acquired in SB502 on the basis of the confidence calculated for each pixel in SB503. The region extracted or region-segmented as the affected-area region 202 will also be referred to as the "estimated area" or the "extracted region".

In this embodiment, as an example of an initial value, a set of pixels having a confidence value of at least 50(%) is extracted as the affected-area region 202. Note that, in SB504, the confidence reference value is not limited to 50(%), and a larger value than 50(%) may be used. Further, the affected-area region 202 is not limited to being extracted on the basis of the confidence as a pressure ulcer and may be extracted on the basis of a combination of the confidence as a pressure ulcer and a confidence relating to a classification class other than the pressure ulcer class. For example, a set of pixels in which, of the confidence values relating to the respective classification classes, the value of the confidence as a pressure ulcer is highest may be extracted as the affected-area region 202. Alternatively, for example, a set of pixels in which the confidence as a pressure ulcer is at least 50(%) and the confidence as a region of normal skin does not exceed 30(%) may be extracted as the affected-area region 202.

In SB505, the size-assessing unit 134 calculates the size of the affected-area region 202 extracted in SB504 on the image data on the basis of information relating to the angle of view or the pixel size of the image data and the distance information generated in SA505. In this embodiment, the size-assessing unit 134 calculates the surface area of the affected-area region 202 as an example of the information relating to the size of the affected-area region.

Figure 6:
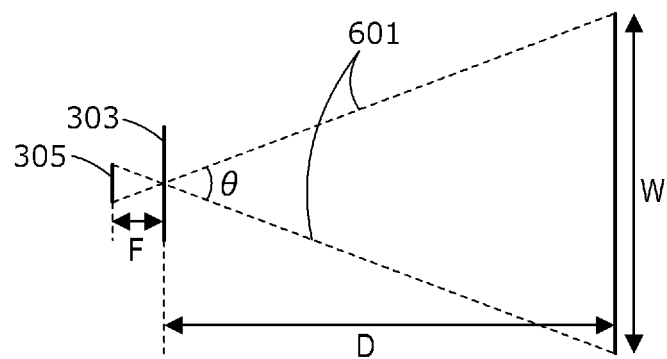
FIG. 6 is a view illustrating an example of a method for calculating the surface region of an affected-area region.

FIG. 6 is a view illustrating an example of a method for calculating the surface area of the affected-area region 202. The imaging apparatus 120 can be handled as a pinhole model such as that shown in FIG. 6. Incident light 601 passes through a principal point of the lens 303 and is received by an imaging plane of the image sensor 305. The distance from the imaging plane to the principal point of the lens corresponds to a focal length F. Here, when a thin lens approximation is used, the two principal points, namely, the front-side principal point and the rear-side principal point, are assumed to coincide. Further, although, on the pinhole model, the lens 303 appears to be a single lens having no thickness, the actual lens may be constituted by a plurality of lenses having thickness and including a focus lens, or by a zoom lens.

By adjusting the focus lens of the lens 303 so that an image is formed on the plane of the image sensor 305, the imaging apparatus 120 adjusts the focus onto the subject 201. When the focal length F can be varied using a zoom lens, an angle of view θ varies. At this time, a width W of the subject 201 on the focal plane is geometrically determined from the relationship between the angle of view θ of the imaging apparatus 120 and a subject distance D. The width W of the subject 201 is calculated using a trigonometric function. In other words, the width W of the subject 201 is determined by the relationship between the angle of view θ, which has the focus position and the zoom amount as parameters, and the subject distance D. By dividing the value of the width W of the subject 201 by the number of pixels on a line of the image sensor 305, which corresponds to the width W, a length on the focal plane corresponding to one pixel on the image is acquired.

The surface area of the affected-area region 202 is calculated as the product of the number of pixels in the affected-area region 202, which is acquired from the result of the region segmentation performed in SB504, and the surface area of one pixel, which is acquired from the length on the focal plane corresponding to one pixel on the image. Note that the width W of the subject 201 or the length on the focal plane corresponding to one pixel on the image may be determined recursively by photographing a subject with a known width W while varying the subject distance D so as to acquire data about the subject. Further, when the subject distance D is singular, the subject must be planar in order to determine the surface area correctly.

The surface area of the affected-area region 202 may be calculated as follows. In SA505, the information-generating unit 125 generates distance information in a plurality of positions on the image surface. In SB505, the size-assessing unit 134 may detect inclination and variation in a depth direction of the subject 201 using the distance information generated by the information-generating unit 125 and calculate the surface area of the affected-area region 202 on the basis of the detected inclination and variation.

Further, the size-assessing unit 134 may calculate the lengths of the major and minor axes and the rectangular area of the affected-area region 202, which are acquired from the result of the region segmentation performed in SB504, and set the results as the surface area of the affected-area region 202. The lengths of the major and minor axes and the rectangular area of the affected-area region 202 can be calculated on the basis of information relating to the angle of view or the pixel size of the image data and the distance information generated in SA505.

In the pressure ulcer assessment index "DESIGN-R", the size of a pressure ulcer is determined by measuring the value of the product of the major and minor axes. In the image processing system according to this embodiment, by analyzing the major and minor axes, compatibility with data measured previously using "DESIGN-R" can be secured. In "DESIGN-R", in mathematical terms, a method of calculating pluralities of major and minor axes is considered. As an example, the size-assessing unit 134 can calculate the length of the long side of a rectangle (a minimum bounding rectangle) having the minimum surface area, among rectangles touching the outside of the affected-area region 202, as the major axis, and calculate the length of the short side thereof as the minor axis.

Further, as another method for calculating the major and minor axes, the maximum Feret diameter, i.e., the maximum caliper length, and the minimum Feret diameter may be selected respectively as the major axis and the minor axis. As a further method for calculating the major and minor axes, the maximum Feret diameter, i.e., the maximum caliper length may be selected as the major axis, and a length measured in an orthogonal direction to the axis of the maximum Feret diameter may be selected as the minor axis. Any desired method may be selected as the method for calculating the major and minor axes on the basis of compatibility with conventional measurement results.

Figure 7:
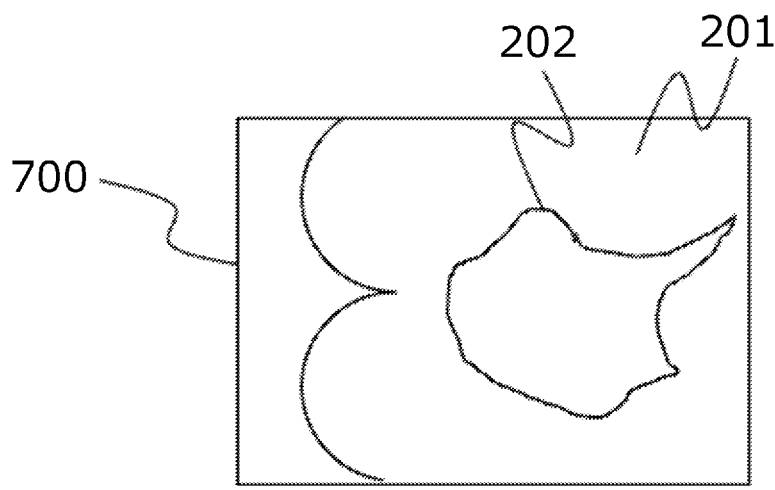
FIG. 7 is a view showing a first example of an image before superimposing the affected-area region.
Figure 8:
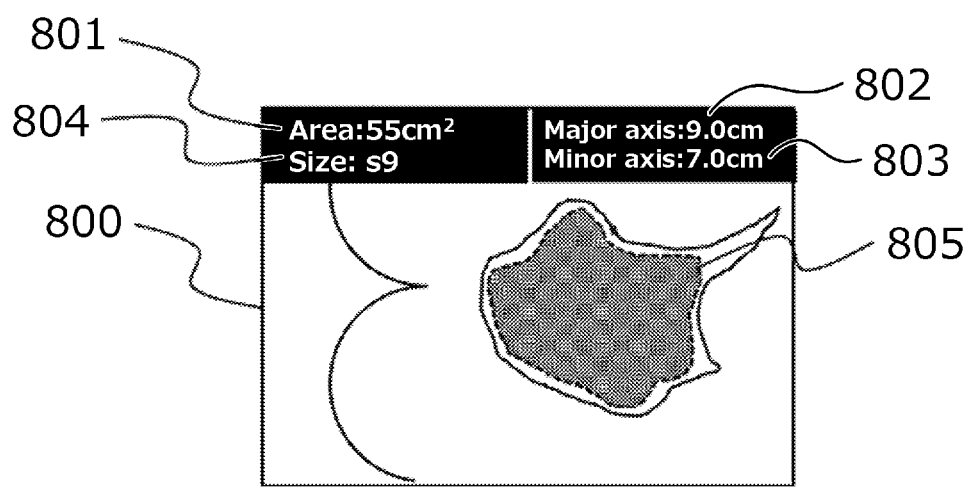
FIG. 8 is a view showing an example of an image on which the affected-area region has been superimposed.

In SB506, the superimposing unit 135 superimposes the information indicating the extracted affected-area region 202 and the information relating to the size of the affected-area region 202 on the image data used to extract the affected-area region 202. Referring to FIGS. 7 and 8, a method for superimposing the information indicating the extracted affected-area region 202 and the information relating to the size of the affected-area region 202 on the image data will be described.

FIG. 7 is a view showing a first example of an image before superimposing the affected-area region. An image 700 corresponds to an image before superimposition processing. The subject 201 and the affected-area region 202 are displayed on the image 700.

FIG. 8 is a view showing an example of an image on which the affected-area region has been superimposed. An image 800 corresponds to an image after the superimposition processing. The information relating to the size of the affected-area region 202 is displayed so as to be superimposed on the upper portion of the image 800. More specifically, a surface area value 801 of the affected-area region 202, a length 802 of the major axis of the affected-area region 202, a length 803 of the minor axis of the affected-area region 202, and an assessment result 804 of the "size" according to "DESIGN-R" are displayed so as to be superimposed on the image 800. Note that as long as the colors of the character strings and the background color of 801 to 804 can be seen clearly, the colors are not limited to white and black. Further, by setting a translucency and performing a blending, it is possible to configure the image so that the part thereof on which the character strings are superimposed remains visible.

An estimated area 805 of the affected-area region 202 extracted (subjected to region segmentation) in SB504 is displayed on the image 800 in a superimposed fashion by a blending. By displaying the estimated area 805 in a superimposed fashion, the user can check whether or not the estimated area 805 extracted as the affected-area region 202 is appropriate. The color of the estimated area 805 is preferably set so as not to overlap the color of the subject 201. The translucency of the a blending is preferably within a range that allows the user to recognize the estimated area 805 and to check the affected-area region 202. Note that the method of superimposing the estimated area 805 is not limited to a blending. For example, the estimated area 805 may be displayed in a superimposed fashion while the entirety thereof blinks, or a line forming the outer edge of the estimated area 805 may be displayed in a superimposed fashion. Note that instead of having the superimposing unit 135 superimpose an image showing the region of the estimated area 805 on the image prior to superimposition in SB506, the imaging apparatus 120 may display an image showing the region of the received estimated area 805 in a superimposed fashion.

In SB507, the second output unit 136 transmits (outputs) the information indicating the affected-area region 202 extracted in SB504 to the imaging apparatus 120. Further, the second output unit 136 outputs the information relating to the size of the affected-area region 202, calculated in SB505, to the imaging apparatus 120. In this embodiment, the image 800 subjected to superimposition processing in SB506 is output to the imaging apparatus 120 by wireless communication.

In SA507, the second acquisition unit 128 acquires, from the image processing apparatus 130, the information relating to the extracted affected-area region 202 and/or the information relating to the size of the affected-area region 202. In this embodiment, the second acquisition unit 128 acquires the superimposition-processed image 800 output by the image processing apparatus 130 in SB507.

In SA508, the display unit 126 displays the superimposition-processed image 800 received in SA507 on the display apparatus 313. The imaging apparatus 120 displays the information indicating the extracted affected-area region 202 and/or the information relating to the size of the affected-area region 202 in a superimposed fashion on the live view image (the image 700) generated by the imaging unit 123. The user of the imaging apparatus 120 can advance to main imaging processing S510 after checking, prior to release, that the information relating to the size of the affected-area region 202 and the estimated area 805 estimated as the affected-area region 202 are appropriate.

In SA509, the system control circuit 310 determines whether or not the release of the operating member 314 has been pressed. When the release has not been pressed, the processing is returned to SA502. When the release has been pressed, the live view processing S500 is terminated, and the processing advances to SA511. The live view processing S500 prior to SA511 is processing for displaying a live view image, whereas the processing of SA511 onward corresponds to the main imaging processing S510 for measuring the information relating to the size of the affected-area region 202 for the final time and recording the image.

S510: Main imaging processing Next, the main imaging processing S510 will be described. The main imaging processing S510 corresponds to the processing of main imaging for extracting the affected-area region 202. The main imaging processing S510 includes processing of SA511 to SA516 performed by the imaging apparatus 120 and processing of SB511 to SB516 performed by the image processing apparatus 130.

In SA511, similarly to SA502, the AF unit 122 performs AF processing in order to focus on the subject 201. Further, the AF unit 122 outputs the distance to the subject 201 from the focus adjustment amount or the movement amount of the focus lens. In SA512, similarly to SA503, the imaging unit 123 captures an image of the subject 201 so as to include the affected-area region 202 of the subject 201.

In SA513, similarly to SA504, the image-processing unit 124 performs development processing and resizing processing. In SA513 of the main imaging processing S510, in comparison with SA504, which is the image processing of the live view processing S500, the precision with which the size of the image and the size of the affected-area region 202 are measured is prioritized over the processing time. As a result, the image-processing unit 124 generates an image resized to a size equaling or exceeding the size of the image generated in SA504. For example, in SA513, the image-processing unit 124 can resize the image to a size of approximately 4.45 megabytes with 1440 pixels×1080 pixels and 4-bit RGB color. Note that as long as the image is resized to a larger size than the size of the image on the live view display, the size of the resized image is not limited thereto.

In SA514, similarly to SA505, the information-generating unit 125 acquires (generates) distance information relating to the distance to the subject 201. In SA515, similarly to SA506, the output unit 127 transmits (outputs) the image data generated in SA513 and the distance information relating to the distance to the subject 201, generated in SA514, to the image processing apparatus 130.

In SB511, similarly to SB502, the acquisition unit 131 receives (acquires) the image data and the distance information relating to the distance to the captured subject 201, output from the imaging apparatus 120.

In SB512, similarly to SB503, the confidence-calculating unit 132 calculates the confidence as a pressure ulcer for each pixel of the image data acquired in SB511 on the basis of the image data. The details of the processing for calculating the confidence are similar to those of the processing of SB503 and have therefore been omitted.

In SB513, similarly to SB504, the extracting unit 133 extracts, or performs region segmentation on, the affected-area region 202 of the subject 201 from the image data acquired in SB511 on the basis of the confidence calculated for each pixel in SB512. The details of the processing for extracting or performing region segmentation on the affected-area region 202 are similar to those of the processing of SB504 and have therefore been omitted.

In SB514, similarly to SB505, the size-assessing unit 134 calculates information relating to the size of the affected-area region 202 extracted in SB513 on the image data on the basis of the distance information generated in SA514. The details of the processing for assessing the size of the affected-area region 202 are similar to those of the processing of SB505 and have therefore been omitted.

In SB515, similarly to SB506, the superimposing unit 135 superimposes the information indicating the extracted affected-area region 202 and the information relating to the size of the affected-area region 202 on the image data used to extract the affected-area region 202. The details of the superimposition processing are similar to those of the processing of SB506, described using FIGS. 7 and 8, and have, therefore, been omitted.

Figure 9:
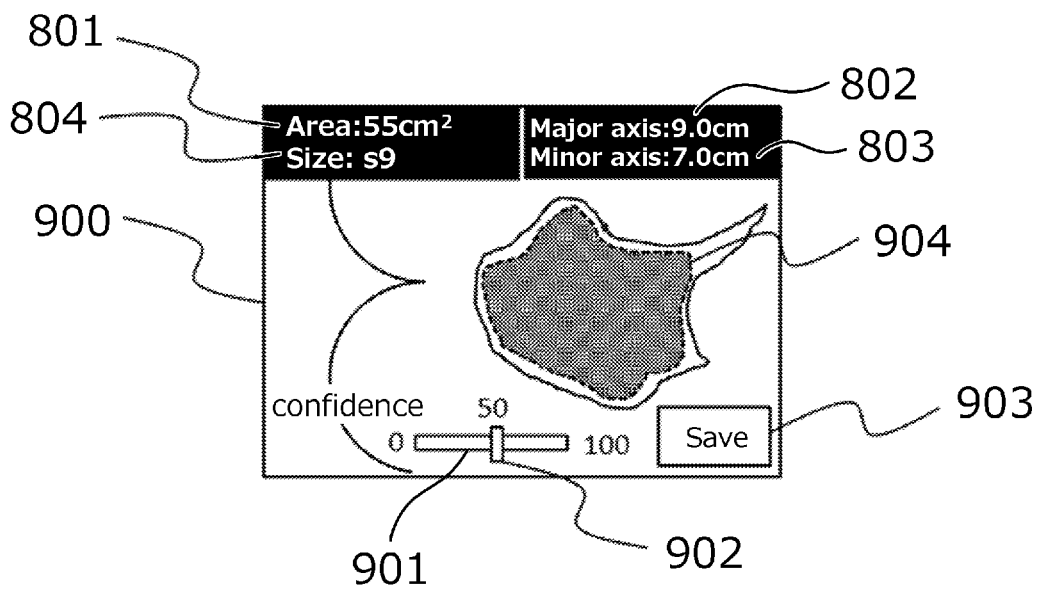
FIG. 9 is a view showing a first example of an image displaying the affected-area region before adjustment.

Here, referring to FIG. 9, a GUI (Graphical User Interface) on which the user modifies the reference value of the confidence as a pressure ulcer will be described. FIG. 9 is a view showing a first example of an image displaying the affected-area region before adjustment. Note that identical display elements to those of FIG. 8 have been allocated identical reference numerals, and a description thereof has been omitted.

In SB515, as shown in FIG. 9, the superimposing unit 135 superimposes a slider 901 for modifying the reference value of the confidence as a pressure ulcer. The slider 901 is used in an operation for modifying the reference value when the user determines, in region adjustment processing S520 to be described below, that s/he wishes to view a different size or shape range to the displayed affected-area region 202.

In the example of FIG. 9, a lower limit value "0" (%) and an upper limit value "100" (%) of the reference value are depicted on the respective ends of the slider 901. Note that the lower limit value and the upper limit value of the reference value are not limited to 0 and 100, and may be limited to a range in which the user is permitted to modify the reference value. A white, vertically elongated rectangle on the slider 901 represents the position of the current set value of the confidence reference value. A current reference value of "50" (%) is depicted above a selecting member 902 for selecting the set value on the slider 901.

Note that, in the example of FIG. 9, the superimposing unit 135 superimposes the slider 901 for modifying the confidence reference value relating to the pressure ulcer classification class, but the superimposing unit 135 may also superimpose a slider for modifying the confidence reference value relating to a classification class other than the pressure ulcer class. For example, when the extracting unit 133 extracts the affected-area region 202 on the basis of a combination with a confidence relating to a classification class other than the pressure ulcer class, the superimposing unit 135 also superimposes a slider for setting a confidence reference value for the other classification class. The other classification classes are the normal skin region and the background region, for example. The GUI for modifying the reference value is not limited to a slider and may be a knob, or the like.

Further, in SB515, the superimposing unit 135 superimposes a button icon 903 on which "Save" is written on the image 900. The button icon 903 is used to advance to SA526, in which an operation for storing the adjusted image is performed, after an operation has been performed to adjust the displayed affected-area region 202 in SA522, to be described below. Note that the character string on the button icon 903 is not limited to "Save", and any character string meaning that the image will be stored may be used. Further, the button icon 903 is not limited to a rectangular shape and may be a circle or the like.

Returning to the description of FIG. 5, in SB516, similarly to SB507, the second output unit 136 transmits (outputs) the information indicating the affected-area region 202 extracted in SB513 to the imaging apparatus 120. Further, the second output unit 136 outputs the information relating to the size of the affected-area region 202, calculated in SB514, to the imaging apparatus 120. In this embodiment, the image 900 subjected to superimposition processing in SB515 is output to the imaging apparatus 120 by wireless communication.

In SA516, similarly to SA507, the second acquisition unit 128 receives (acquires), from the image processing apparatus 130, the information relating to the extracted affected-area region 202. In this embodiment, the second acquisition unit 128 acquires the superimposition-processed image 900 output by the image processing apparatus 130 in SB516.

S520: Region Adjustment Processing

Next, the region adjustment processing S520 will be described. The region adjustment processing S520 is processing for adjusting the affected-area region 202 of the image displayed on the display apparatus 313 (the display unit 126) of the imaging apparatus 120 on the basis of a user operation. The image processing apparatus 130 can use the adjusted affected-area region 202 as a surface area measurement subject.

Figure 10:
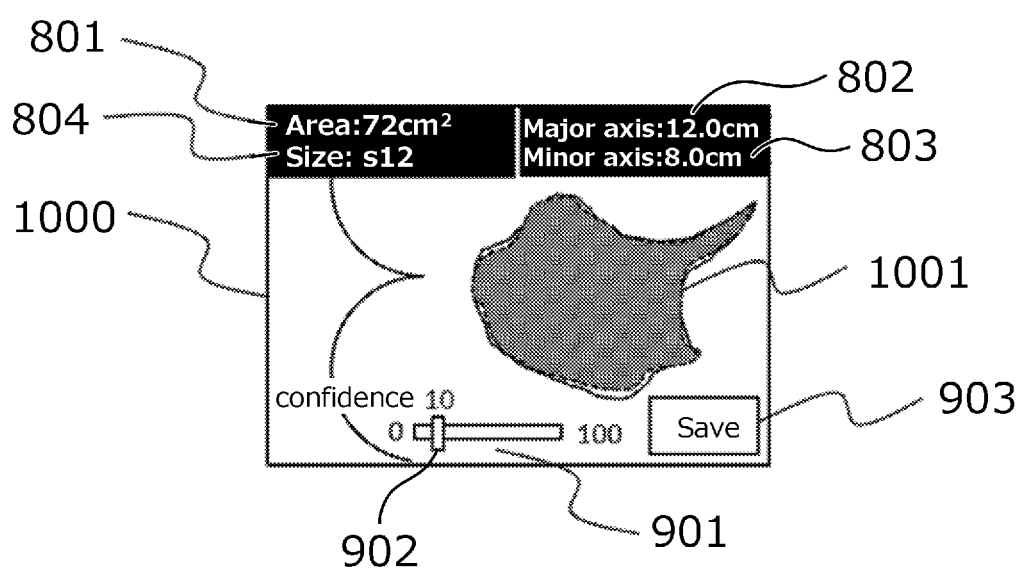
FIG. 10 is a view showing a first example of an image displaying the affected-area region after adjustment.

The region adjustment processing S520 includes processing of SA521 to SA525 performed by the imaging apparatus 120 and processing of SB521 to SB525 performed by the image processing apparatus 130. The processing of the region adjustment processing S520 will be described with reference to FIGS. 9 and 10 as appropriate. FIG. 9 is a view showing a first example of an image displaying the affected-area region before adjustment. FIG. 10 is a view showing a first example of an image displaying the affected-area region after adjustment. Note that, in FIG. 10, identical display elements to those of FIGS. 8 and 9 have been allocated identical reference symbols.

In SA521, similarly to SA508, the display unit 126 displays the superimposition-processed image 900 (FIG. 9) acquired in SA516 or SA525 on the display apparatus 313. In SA521, in contrast to SA508, the display unit 126 adjusts the range of the estimated area 805 (the region to be subjected to surface area measurement) of the affected-area region 202 displayed on the image 900 on the basis of a user operation. The user can adjust the range of the estimated area 805 of the affected-area region 202 using the operating member 314.

In this embodiment, it is assumed that a touch panel display on the display apparatus 313 is used as an operating means for adjusting the region to be subjected to surface area measurement. The user can adjust the region by performing a touch operation on the screen of the display apparatus 313. Note that the operating means for adjusting the region is not limited to a touch panel display, and a button, a lever, or the like, provided on the imaging apparatus 120 may be used instead.

In SA522, the reference-value-modifying unit 121 determines whether or not the reference value has been modified by a user operation in relation to the image 900 displayed in SA521. When the reference value has been modified, the processing advances to SA523, and when the reference value has not been modified, the processing advances to SA526.

Here, referring to FIG. 9, an example of a method for adjusting the region will be described. It is assumed that the reference value of the confidence as a pressure ulcer has been set at an initial value of 50(%). In SA521, an estimated area 904 of the affected-area region 202 with a reference value of at least 50(%) is displayed so as to be superimposed on the image 900.

When the estimated area 904 is close to the pressure ulcer region envisaged by the user, the user taps the button icon 903 without adjusting the region. Since the reference value is not modified, the processing advances to SA526.

When, on the other hand, the estimated area 904 is smaller or larger than the pressure ulcer region envisaged by the user, the user operates the slider 901 in order to adjust the estimated area 904. The user adjusts the estimated area 904 by moving the selecting member 902 of the slider 901 either left or right. When the slider 901 is operated, the reference is modified, and, therefore, the processing advances to SA523.

In SA523, the reference-value-modifying unit 121 modifies the reference value of the confidence as a pressure ulcer in accordance with the position of the selecting member 902 of the slider 901, operated by the user in SA522. In FIG. 10, for example, the selecting member 902 of the slider 901 is moved by a user operation to a position of 10(%). Accordingly, the reference value of the confidence as a pressure ulcer is modified to 10(%). In this case, by reducing the reference value, an estimated area 1001 of the affected-area region 202 is enlarged on an image 1000 to a larger range than that of the estimated area 904 shown in FIG. 9.

Note that the classification class in which the reference value is modified is not limited to the pressure ulcer class. For example, respective confidence reference values may be modified with respect to a plurality of classification classes corresponding to a "normal skin region" and skin diseases or conditions other than pressure ulcers, such as a "bruise" and a "scratch". Furthermore, when confidence values relating to a plurality of classification classes are combined, the reference value may be set in relation to a ratio of the confidence as a pressure ulcer to the confidence as a normal skin region, for example.

In SA524, the output unit 127 transmits (outputs) information relating to the confidence reference value modified in SA523 to the image processing apparatus 130.

In SB521, the acquisition unit 131 acquires the information relating to the modified confidence reference value, output from the imaging apparatus 120.

Next, in SB522, the extracting unit 133 extracts, or performs region segmentation on, the affected-area region 202 based on the modified reference value (the adjusted estimated area 1001) from the image data acquired in SB511. The extracting unit 133 can extract, or perform region segmentation on, the affected-area region 202 on the basis of the confidence calculated for each pixel in SB512 and the information relating to the confidence reference value modified in SA523. When the reference value is modified to a higher value, the affected-area region 202 becomes smaller, and when the reference value is modified to a lower value, the affected-area region 202 becomes larger Note that the affected-area region 202 is not limited to being extracted on the basis of the confidence as a pressure ulcer. For example, the extracting unit 133 may extract, as the affected-area region 202, a region other than the region in which the confidence as a normal skin region equals or exceeds the reference value. Further, the affected-area region 202 may be adjusted by combining reference values relating to a plurality of classification classes so that, for example, the reference value of the confidence as a normal skin region is no higher than 30 and the reference of the confidence as a pressure ulcer equals or exceeds 80.

In SB523, similarly to SB505, the size-assessing unit 134 calculates information relating to the size of the affected-area region 202 extracted in SB522 on the basis of the distance information generated in SA514. The details of the processing for calculating the information relating to the size of the affected-area region 202 are similar to those of the processing of SB505 and have therefore been omitted.

In SB524, similarly to SB515, the superimposing unit 135 superimposes the information indicating the extracted affected-area region 202 and the information relating to the size of the affected-area region 202 on the image data used to extract the affected-area region 202. The superimposing unit 135 also superimposes the button icon 903 and the slider 901 on the image data. The details of the superimposition processing are similar to those of the processing of SB506 and SB515, described using FIGS. 7 and 8, and have therefore been omitted.

Note, however, that in SB524, as indicated by the image 1000 shown in FIG. 10, the superimposing unit 135 performs superimposition after modifying the position of the selecting member 902 of the slider 901 to a position corresponding to the value of the reference value modified in SA523. FIG. 10 shows a case in which the confidence reference value is modified from 50(%) to 10(%) in SA523.

In SB525, similarly to SB507, the second output unit 136 transmits (outputs) the information indicating the affected-area region 202 extracted in SB522 to the imaging apparatus 120. Further, the second output unit 136 outputs the information relating to the size of the affected-area region 202, calculated in SB523, to the imaging apparatus 120. In this embodiment, the image 1000 subjected to superimposition processing in SB524 is output to the imaging apparatus 120 by wireless communication.

In SA525, similarly to SA507, the second acquisition unit 128 receives (acquires), from the image processing apparatus 130, the information relating to the extracted affected-area region 202. In this embodiment, the second acquisition unit 128 acquires the superimposition-processed image 1000 output by the image processing apparatus 130 in SB525. The processing then returns to SA521, where the display unit 126 displays the information relating to the affected-area region 202, acquired in SA525, on the display apparatus 313.

In SA526, the storage unit 129 stores the information relating to the affected-area region 202, displayed in SA521, in the external memory I/F 312 of the imaging apparatus 120, whereupon the processing shown in FIG. 5 is terminated.

Actions and Effects of First Embodiment According to this embodiment, as described above, the imaging apparatus 120 captures an image of the subject and modifies the reference value of the confidence as a pressure ulcer on the basis of a user operation. The image processing apparatus 130 then analyzes the captured image, extracts a set of pixels exceeding the confidence reference value modified by the user as the affected-area region 202, and superimposes the extracted region on the captured image. The imaging apparatus 120 displays the image with the affected-area region 202 superimposed thereon on the display apparatus 313. The user (a healthcare worker such as a doctor), when assessing the size of a pressure ulcer, for example, can make fine adjustments to the region to be subjected to surface area calculation by modifying the reference value with respect to the affected-area region 202 extracted by the image processing system 100 on the basis of the reference value of the confidence as a pressure ulcer. In border parts where there is little variation in the confidence as a pressure ulcer, the border is often visually ambiguous and unusually shaped, and therefore the user can prioritize adjustments relating to whether or not these border parts are to be extracted as the affected-area region 202. Further, on the basis of operations of the operating member 314, the user can adjust the affected-area region 202 interactively while checking the border of the extracted affected-area region 202.

Furthermore, at present, the size of a pressure ulcer is acquired as the product of the major and minor axes of the pressure ulcer, but by calculating the surface area of the affected-area region of the pressure ulcer using the image processing apparatus 130 according to this embodiment, the severity of the pressure ulcer can be assessed more accurately.

Second Embodiment

Next, a second embodiment will be described. In the first embodiment, the imaging apparatus 120 includes the reference-value-modifying unit 121, and the reference value of the confidence as a pressure ulcer can be modified by a user operation. In this embodiment, on the other hand, the confidence value of a pixel selected by the user is acquired, and the affected-area region 202 is extracted using the acquired value as the confidence reference value. More specifically, the affected-area region 202 is extracted so that the border thereof is formed by pixels having identical confidence values to the pixel selected by the user.

In this embodiment, as noted above, the processing that differs from the first embodiment is mainly the processing for setting the reference value and processing for extracting the affected-area region 202 on the basis of the confidence of the pixel selected by the user. In the description of this embodiment, identical configurations and processing to the first embodiment have been allocated identical reference symbols to those used in FIGS. 1 to 10, and a detailed description thereof has been omitted.

Figure 11:
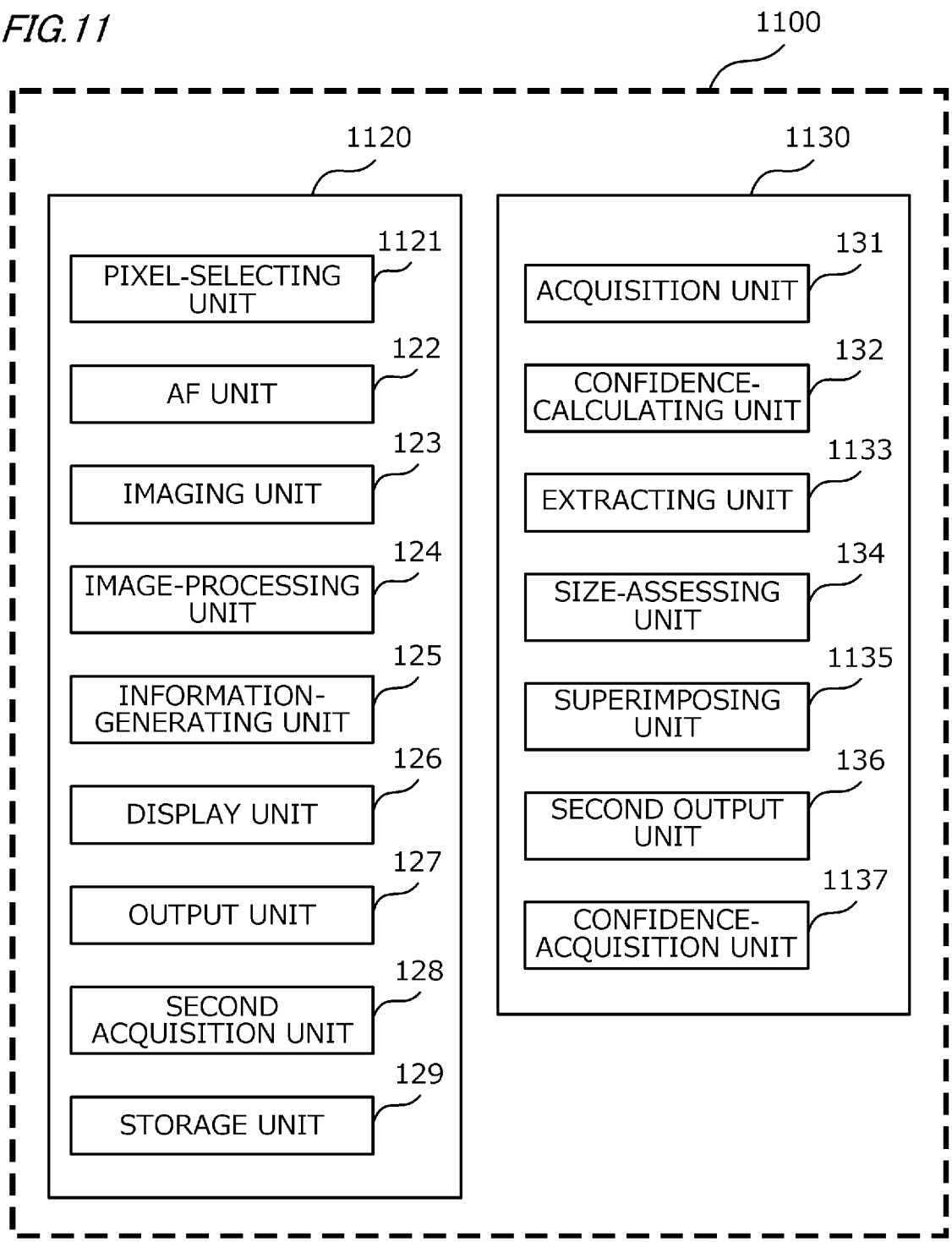
FIG. 11 is a view showing an example functional configuration of an image processing system of a second embodiment.

Functional Configuration and Hardware Configuration FIG. 11 is a view showing an example functional configuration of an image processing system according to the second embodiment. An image processing system 1100 of this embodiment differs from the image processing system 100 of the first embodiment as follows. In the image processing system 1100 of this embodiment, an imaging apparatus 1120 includes pixel-selecting unit 1121 instead of the reference-value-modifying unit 121. An image processing apparatus 1130 includes confidence-acquisition unit 1137. Further, extracting unit 1133 and superimposing unit 1135 of the image processing apparatus 1130 execute different processing content to the extracting unit 133 and superimposing unit 135 of the first embodiment. The imaging apparatus 1120 and the image processing apparatus 1130 can realize the processing of this embodiment using identical hardware configurations (see FIGS. 3 and 4) to those of the imaging apparatus 120 and image processing apparatus 130 of the first embodiment.

The pixel-selecting unit 1121 of the imaging apparatus 1120 acquires the position of the pixel selected by the user. The confidence of the selected pixel as a pressure ulcer is used as the confidence reference value for extracting the affected-area region 202.

The confidence-acquisition unit 1137 of the image processing apparatus 1130 acquires the confidence of the pixel selected by the pixel-selecting unit 1121 as a pressure ulcer. The extracting unit 1133 extracts the affected-area region 202 on the basis of the position of the pixel selected by the pixel-selecting unit 1121 and the confidence value acquired by the confidence-acquisition unit 1137. The superimposing unit 1135 superimposes the information indicating the extracted affected-area region 202 and the information relating to the size of the affected-area region 202 on the image data used to extract the affected-area region 202.

Other functional configurations of the image processing system 1100 (the imaging apparatus 1120 and the image processing apparatus 1130) correspond to the functional configurations of the image processing system 100 of the first embodiment.

Figure 12:
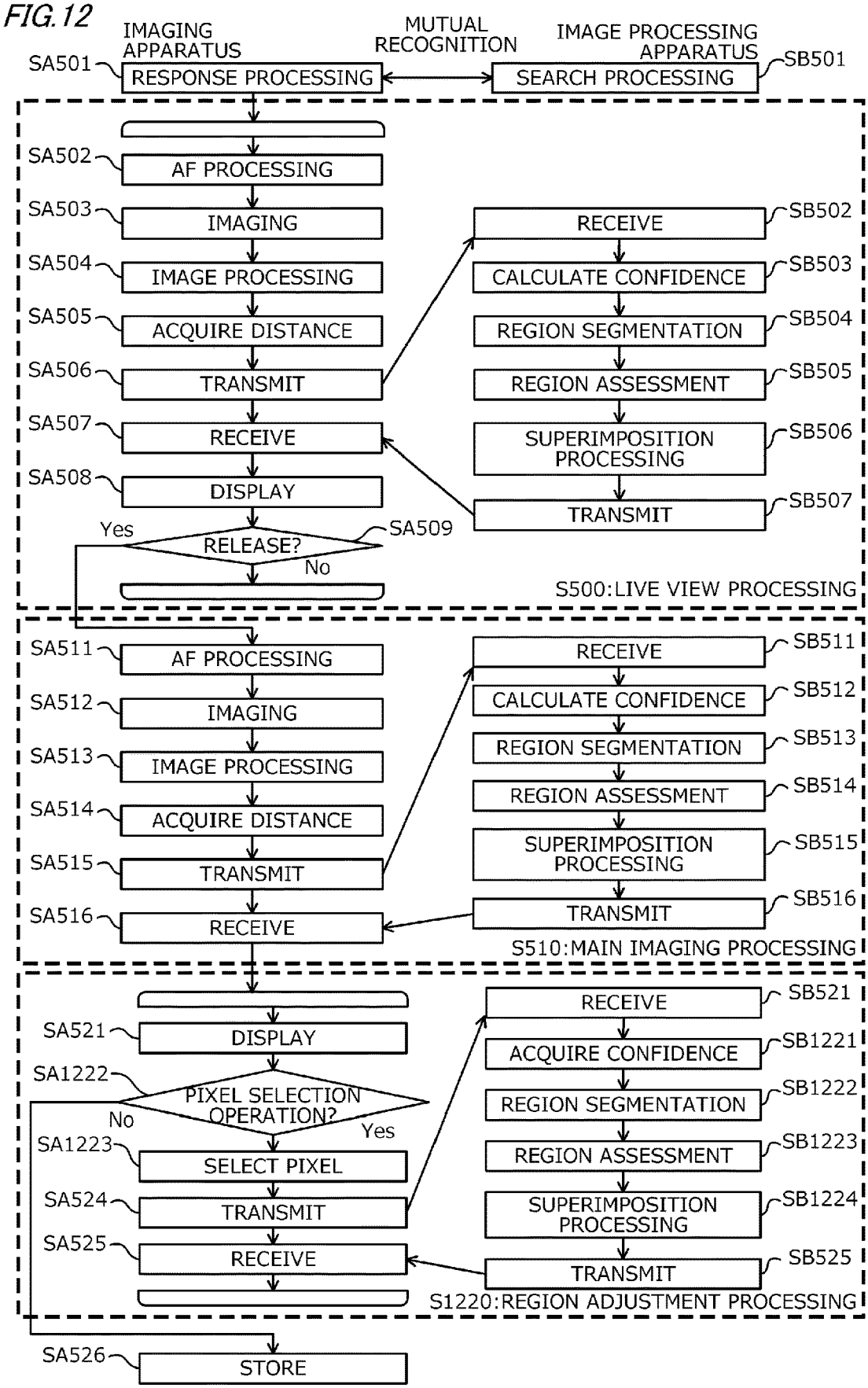
FIG. 12 is a view illustrating an example operation of the image processing system of the second embodiment.
Figure 13:
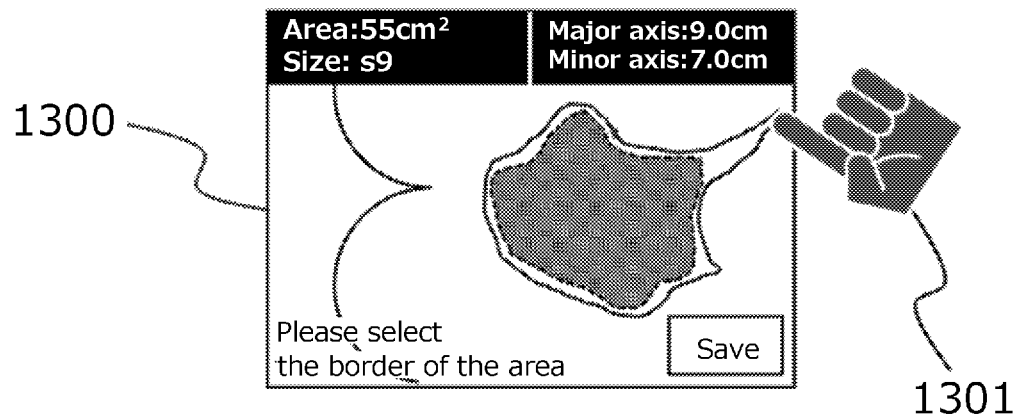
FIG. 13 is a view showing a second example of an image displaying the affected-area region before adjustment.
Figure 14:
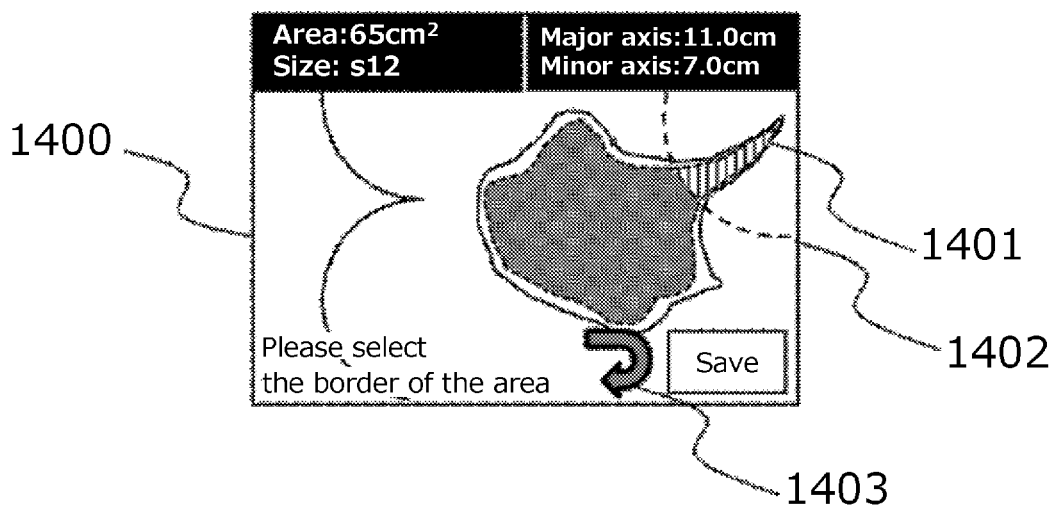
FIG. 14 is a view showing a second example of an image displaying the affected-area region after adjustment.
Figure 15:
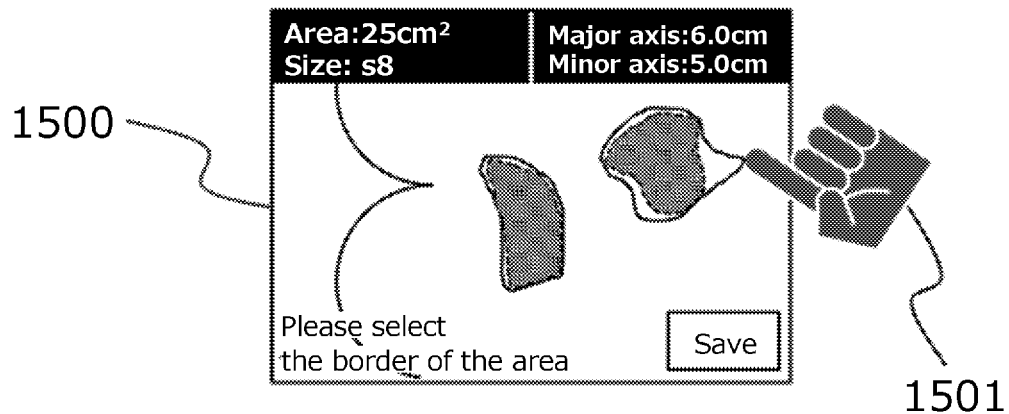
FIG. 15 is a view showing a third example of an image displaying the affected-area region before adjustment.
Figure 16:
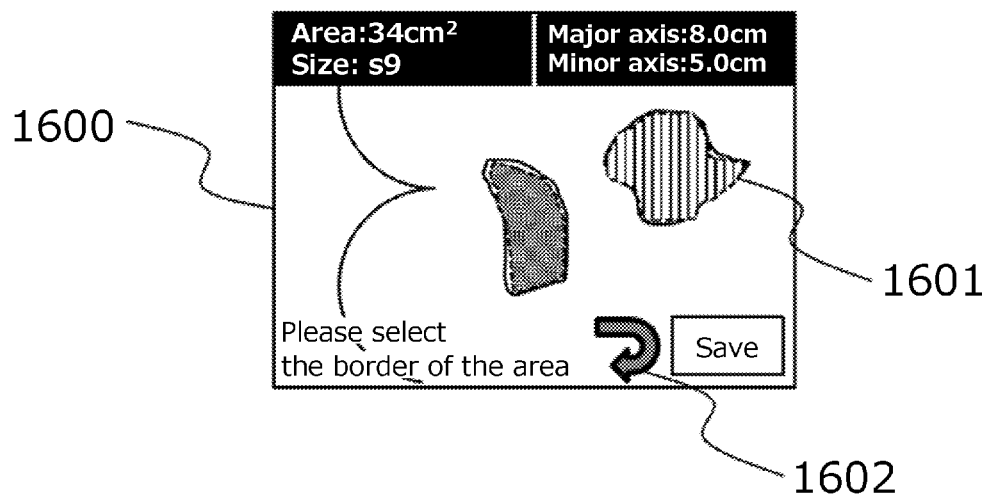
FIG. 16 is a view showing a third example of an image displaying the affected-area region after adjustment.

Operation of Image Processing System Referring to FIGS. 12 to 16, an operation of the image processing system 1100 according to this embodiment will be described. FIG. 12 is a view illustrating an example operation (an example of processing executed according to a flowchart) of the image processing system 1100 according to the second embodiment. On the flowchart shown in FIG. 12, region adjustment processing 1220 partially differs from the region adjustment processing 520 of the first embodiment (FIG. 5). FIGS. 13 and 14 are views showing second examples of images displaying the affected-area region before and after adjustment. FIGS. 15 and 16 are views showing third examples of images displaying the affected-area region before and after adjustment.

The flowchart of the imaging apparatus 1120 of this embodiment differs from the flowchart of the imaging apparatus 120 of the first embodiment in that the processing of SA522 and SA523 is replaced with processing of SA1222 and SA1223.

The processing executed by the imaging apparatus 1120 is realized by having the system control circuit 310 expand a program stored in the nonvolatile internal memory 311 in the system memory (the RAM) and execute the program. The processing executed by the image processing apparatus 1130 is realized by having the CPU 410 expand a program stored in the ROM of the main storage apparatus 421 in the system memory and execute the program. Note that the processing of FIG. 12 is started when power is supplied to the imaging apparatus 1120 and the imaging apparatus 1120 responds to search processing executed by the image processing apparatus 1130.

In SA521, a superimposition-processed image 1300 (FIG. 13) acquired in SA516 or SA525 is displayed by the display unit 126. In SA1222, the pixel-selecting unit 1121 determines whether or not the user has performed an operation to select a pixel using the operating member 314. When the user has performed an operation to select a pixel, the processing advances to SA1223. When the user has not performed an operation to select a pixel, the processing advances to SA526.

In SA1223, the pixel-selecting unit 1121 acquires the position of a specific pixel selected by the user on the image 1300 using the operating member 314. The user can select a specific pixel on the image 1300 using the touch panel display of the display apparatus 313, for example, as the operating member 314. In other words, the user selects a specific pixel on the image 1300 by tapping the screen of the display apparatus 313. In the following description, the pixel selected by the user will also be referred to as the "user-selected pixel".

In the example of FIG. 13, the user taps a part determined by the user to be the border of the affected-area region 202 using a hand 1301, and, as a result, the pixel-selecting unit 1121 can acquire the position of a pixel set as the border of the affected-area region 202. Note that the operating unit for selecting a pixel on the image 1300 is not limited to a touch panel display and may be a button, or the like, provided on the imaging apparatus 1120.

On the flowchart of the image processing apparatus 1130 of this embodiment, the processing content of SB1221 to SB1224 differs from the processing content of SB522 to SB524, executed by the image processing apparatus 130 of the first embodiment.

In SB1221, the confidence-acquisition unit 1137 acquires the confidence as a pressure ulcer, calculated in SB512, in relation to the pixel selected in SA1223. The acquired confidence is used as the reference value for extracting the affected-area region 202.

In SB1222, the extracting unit 1133 extracts, or performs region segmentation on, the affected-area region 202 of the subject 201 from the image data acquired in SB521. The affected-area region 202 is extracted on the basis of the confidence calculated for each pixel in SB512, the position of the user-selected pixel, acquired in SA1223, and the confidence acquired in relation to the user-selected pixel in SB1221.

The extracting unit 1133 extracts a region, within a circle having a radius r (where r is a constant) and centering on the position of the user-selected pixel acquired in SA1223, as the affected-area region 202 using the confidence of the user-selected pixel as the reference value. Further, in relation to a region outside the circle, the extracting unit 1133 re-extracts the affected-area region 202 using the reference value used in SB513. In other words, with regard to the pixels in the circle having the radius r, the extracting unit 1133 extracts, as the affected-area region 202, a set of pixels in which the confidence of each pixel, calculated in SB512, equals or exceeds the confidence of the user-selected pixel acquired in SB1221. Further, with regard to the pixels outside the circle having the radius r, the extracting unit 1133 re-extracts, as the affected-area region 202, a set of pixels in which the confidence of each pixel, calculated in SB512, equals or exceeds 50(%).

In the example of an image 1400 shown in FIG. 14, a region 1401 is a partial region that is re-extracted using the confidence of the pixel selected by the user on the image 1300 as the reference value. A dotted line 1402 shown in FIG. 14 indicates the circumference of a circle having the radius r and centering on the position of the pixel touched (selected) by the hand 1301 of the user in FIG. 13. The partial region partially overlaps the affected-area region 202.

Re-extraction of the affected-area region 202 is not limited to the method shown in FIG. 14, in which pixels equaling or exceeding the confidence of the user-selected pixel are re-extracted from among the pixels within the circle having the radius r and centering on the position of the user-selected pixel. For example, the extracting unit 1133 re-extracts pixels in a partial region (for example, a circle with a radius r/2) that is closer to the user-selected pixel from among the pixels within the circle having the radius r using the confidence of the user-selected pixel as the reference value. In the region outside the partial region, the reference value may be maintained at the value prior to modification, i.e. 50(%).

The re-extraction range is not limited to a circle having the radius r, and the extracting unit 1133 may re-extract pixels having a higher confidence than the user-selected pixel from among the pixels on the image 1300. Alternatively, the extracting unit 1133 may re-extract pixels from a square partial region centering on the user-selected pixel.

In the example of an image 1500 shown in FIG. 15, the affected-area region 202 is divided into two regions. In this case, the extracting unit 1133 may perform re-extraction on the partial region that is closer to the pixel selected by a hand 1501 of the user. For example, the extracting unit 1133 determines whether or not the confidence in a closed partial region that includes pixels with a confidence of within approximately 30(%) of the confidence of the user-selected pixel equal or exceed the confidence of the user-selected pixel (the reference value).

In the example of an image 1600 shown in FIG. 16, a region 1601 denotes the affected-area region 202 re-extracted on the basis of the confidence of the user-selected pixel in relation to an estimated area close to the pixel selected by the hand 1501 of the user on the image 1500. In the region outside the partial region, i.e., the region not selected by the user, re-extraction may be performed on the basis of the confidence prior to re-extraction.

In SB1224 of FIG. 12, similarly to SB506, the superimposing unit 1135 first superimposes the information indicating the extracted affected-area region 202 and the information relating to the size of the affected-area region 202. The details of the superimposition processing are similar to those of the processing of SB506 and have therefore been omitted.

Further, in SB1224, the superimposing unit 1135 superimposes an icon 1403 shown in FIG. 14 and an icon 1602 shown in FIG. 16 on the image 1400 and the image 1600, respectively. When the user touches the icon 1403 and the icon 1602, the re-extracted affected-area region 202 displayed in SA521 is returned to the display of the affected-area region 202 prior to re-extraction.

Actions and Effects of Second Embodiment According to this embodiment, as described above, the image processing apparatus 1130 acquires the confidence value of a pixel selected by the user as a pressure ulcer and sets the acquired value as the confidence reference value. The image processing apparatus 1130 then re-extracts the affected-area region 202 from a region on the periphery of the pixel selected by the user. Hence, in this embodiment, the following effects are achieved in addition to the effects described in the first embodiment. The user, when assessing the size of the pressure ulcer, can partially modify the extracted region with respect to the affected-area region 202 that was extracted using a reference value of 50(%), for example, as an initial value. More specifically, when the user notices that a region determined to be the pressure ulcer exists outside the extracted region, the user can select a position (a pixel) determined to be the pressure ulcer, and, in so doing, add a part that the user believes to be the pressure ulcer to the affected-area region 202 in a region on the periphery of the selected position.

The user can thus adjust the extracted region intuitively. Moreover, the affected-area region 202 can be re-extracted on the periphery of a border part that differs from the determination of the user, thereby ensuring that the border part that aligns with the determination of the user is not affected by the correction.

Third Embodiment

Next, a third embodiment will be described. In this embodiment, an image of the subject and information relating to an affected-area region determined by the user to be an appropriate region are registered in a database of the image processing apparatus. By having the image processing apparatus retrain the learning model on the basis of the information in the database, the precision of the confidence-calculating unit can be improved. Further, by having the image processing apparatus modify the confidence reference value used for extraction on the basis of the information in the database, the precision of the extracting unit can be improved.

This embodiment includes, in addition to the configurations of the first and second embodiments, configurations and processing for storing information relating to an affected-area region determined by the user to be appropriate in the database, and for improving the precision of the next region segmentation operation. In the description of this embodiment, identical configurations and processing to the first and second embodiments have been allocated identical reference symbols to those used in FIGS. 1 to 16, and detailed description thereof has been omitted.

Figure 17:
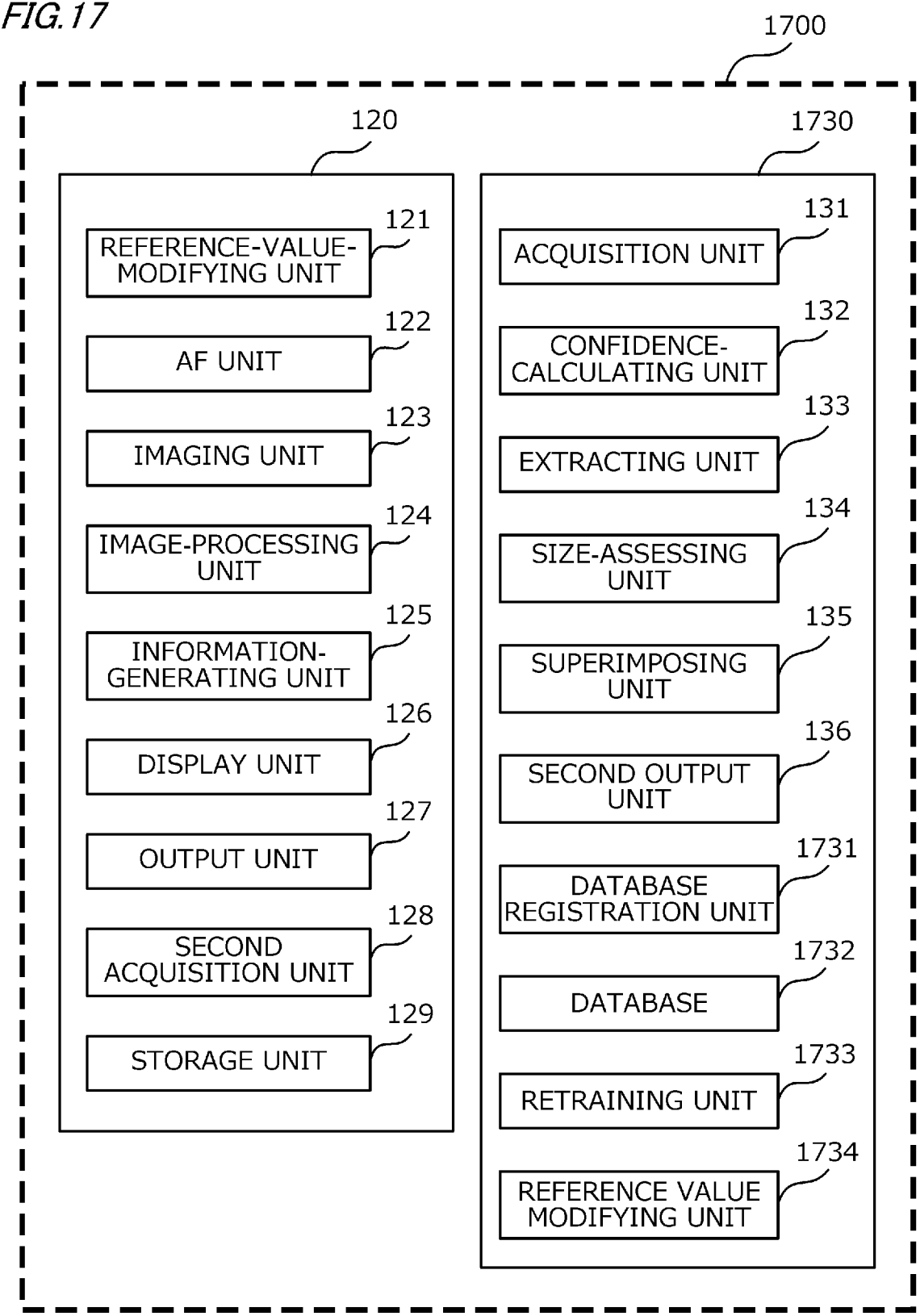
FIG. 17 is a view showing an example functional configuration of an image processing system of a third embodiment.

Functional Configuration and Hardware Configuration FIG. 17 is a view showing an example functional configuration of an image processing system according to the third embodiment. An image processing system 1700 of this embodiment differs from the image processing system 100 of the first embodiment as follows. In the image processing system 1700 of this embodiment, an image processing apparatus 1730 includes a database registration unit 1731, a database 1732, a retraining unit 1733, and a reference-value-modifying unit 1734. The image processing apparatus 1730 can realize the processing of this embodiment using an identical hardware configuration (see FIG. 4) to that of the image processing apparatus 130 of the first embodiment.

The database registration unit 1731 generates a record including the following information and registers the generated record in the database 1732 provided in the image processing apparatus 1730.

The affected area image 700.

The affected-area region 202 extracted by the extracting unit 133.

Information relating to the size calculated by the size-assessing unit 134.

The confidence reference value modified by the reference-value-modifying unit 121 (when the reference value is not modified, the confidence reference value used by the extracting unit 133 in SB504 and SB513).

The database 1732 is used to register records generated by the database registration unit 1731. The retraining unit 1733 retrains the classification model used by the confidence-calculating unit 132 on the basis of the records registered in the database 1732. The reference-value-modifying unit 1734 modifies the confidence reference value used by the extracting unit 133 on the basis of the records registered in the database 1732.

Figure 18:
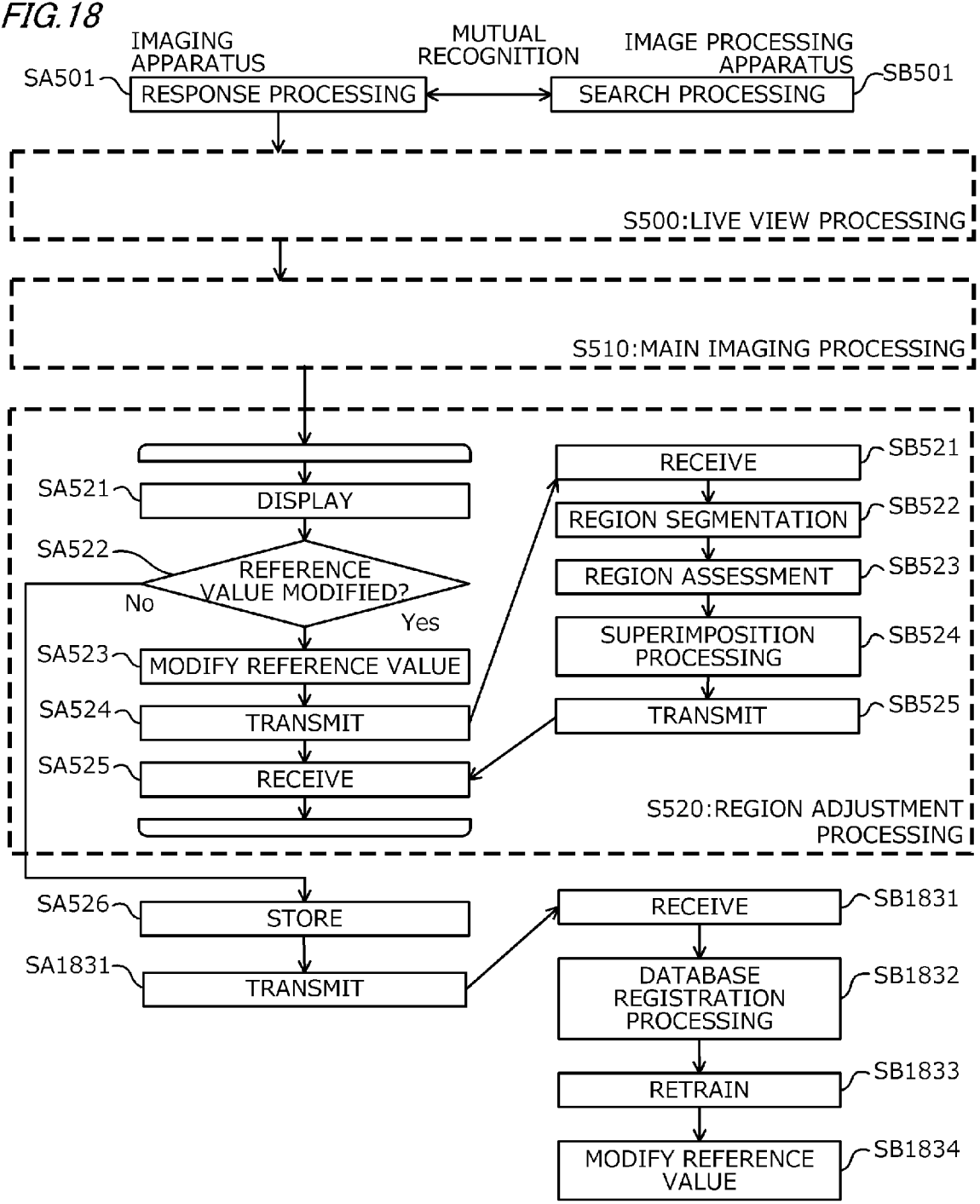
FIG. 18 is a view illustrating an example operation of the image processing system of the third embodiment.

Operation of Image processing System Referring to FIG. 18, an operation of the image processing system 1700 according to this embodiment will be described. FIG. 18 is a view illustrating an example operation (an example of processing executed according to a flowchart) of the image processing system 1700 according to the third embodiment. The live view processing S500 (detailed illustration of which has been omitted), the main imaging processing S510 (detailed illustration of which has been omitted), and the region adjustment processing S520 of the image processing system 1700 are identical to the processing of the first embodiment, shown in FIG. 5, and, therefore, a description thereof has been omitted.

On the flowchart of the imaging apparatus 120 of this embodiment, processing of SA1831 has been added to the flowchart of the imaging apparatus 120 of the first embodiment, shown in FIG. 5. In SA1831, the output unit 127 transmits (outputs) to the image processing apparatus 1730 information indicating that the affected-area region 202 displayed in SA521 has been determined to be appropriate.

On the flowchart of the image processing apparatus 1730 of this embodiment, processing of SB1831 to SB1834 has been added to the workflow of the image processing apparatus 130 of the first embodiment, shown in FIG. 5. In SB1831, the acquisition unit 131 acquires the information output from the imaging apparatus 120 in SA1831.

The processing executed by the imaging apparatus 120 is realized by having the system control circuit 310 expand a program stored in the nonvolatile internal memory 311 in the system memory (the RAM) and execute the program. The processing executed by the image processing apparatus 1730 is realized by having the CPU 410 expand a program stored in the ROM of the main storage apparatus 421 in the system memory and execute the program. Note that the processing of FIG. 18 is started when power is supplied to the imaging apparatus 120 and the imaging apparatus 120 responds to search processing executed by the image processing apparatus 1730.

In SB1832, the database registration unit 1731 generates a record including the following information and registers the generated record in the database 1732 provided in the image processing apparatus 1730.

The affected area image 700 captured in SA512.

The affected-area region 202 finally extracted by the extracting unit 133 in SB513 or SB522.

The information relating to the size finally calculated by the size-assessing unit 134 in SB514 or SB523.

The confidence reference value modified by the reference-value-modifying unit 121 in SA523 (when SA523 is not executed so that the reference value is not modified, the confidence reference value used by the extracting unit 133 in SB504 and SB513).

When the reference value has never been modified in SA523, the database registration unit 1731 need not register a record in the database 1732. Note that, when the reference value has never been modified in SA523, information indicating that the affected-area region 202 displayed in SA521 has been determined to be appropriate need not be transmitted to the image processing apparatus 1730 in SA1831 of the imaging apparatus 120.

In SB1833, the retraining unit 1733 retrains the classification model used by the confidence-calculating unit 132 in SB503 and SB512 on the basis of the record registered in the database 1732. In other words, the retraining unit 1733 generates a trained model by training the model of the neural network using the image registered in the database 1732 and the adjusted affected-area region 202 extracted by the extracting unit 133 as training data.

The training data used for training are not limited to the record registered in the database 1732 in SB1832. For example, the training data used for training may include the training data set used to generate the trained model prior to retraining in addition to the record registered in the database 1732 in SB1832. Further, among the records registered in the database 1732, the records used for training may be limited to records in which the reference value has been modified at least once in SA523.

The learning method used during deep learning is not limited to a case in which learning is performed in the image processing system 1700 from scratch using the data registered in the database 1732. For example, the retraining unit 1733 may retrain the trained model used by the confidence-calculating unit 132 by transfer-learning an existing learning model for assessing the affected-area region 202 in relation thereto. The learning processing performed during deep learning is executed by, for example, a GPU included in the auxiliary calculation apparatus 450, the GPU being good at executing product-sum operations in parallel. The learning processing performed during deep learning may also be executed by an FPGA, an ASIC, or the like, or by an external apparatus.

In SB1834, the reference-value-modifying unit 1734 modifies the confidence reference value used by the extracting unit 133 in SB504 and SB513 on the basis of the records registered in the database 1732. More specifically, an average value of the modified confidence reference values modified in SA523 in relation to all of the images registered in the database 1732 is calculated, and the average value is stored as the confidence reference value to be used subsequently by the extracting unit 133 in SB504 and SB513. When calculating the average value, the confidence reference value of a record that was registered without executing SA523 may be set as the confidence reference value used by the extracting unit 133 in SB504 and SB513.

Note that the confidence reference value to be used subsequently by the extracting unit 133 in SB504 and SB513 is not limited to the average value of the confidence reference values in the respective records in the database 1732, and the median or the mode, for example, may be used instead.

Actions and Effects of Third Embodiment According to this embodiment, as described above, the image processing apparatus 1730 registers an image of the subject 201 and information relating to the affected-area region 202 determined by the user to be an appropriate region in the database 1732. The image processing apparatus 1730 can then modify the confidence reference value used by the extracting unit 133 by retraining the learning model used by the confidence-calculating unit 132 on the basis of the information registered in the database 1732.

Hence, in this embodiment, the following effects are achieved in addition to the effects described in the first embodiment. When the user (a doctor) assesses the size of the pressure ulcer, the image processing apparatus 1730 can retrain the learning model on the basis of information about the appropriate affected-area region 202 that has been adjusted by a user operation. As a result, it is possible to improve the precision with which the affected-area region 202 of the pressure ulcer is extracted from the next captured image onward.

Further, when the user (a doctor) adjusts the affected-area region 202, the image processing apparatus 1730 can store a trend of the modifications to the confidence reference value (for example, the average value of the difference from the current reference value) in the database 1732. By adjusting the reference value in accordance with the trend of the modifications performed by the user, the image processing apparatus 1730 can further improve the precision with which the affected-area region 202 is extracted from the next captured image onward. This embodiment may also be applied to the second embodiment.

Fourth Embodiment

Next, a fourth embodiment will be described. An image processing system of this embodiment incudes a CT scanner instead of the imaging apparatus. Accordingly, the image processing apparatus acquires a CT image generated by the CT scanner and extracts the affected-area region from the CT image, whereupon fine adjustments can be made to the affected-area region through a user operation. This embodiment differs from the first to third embodiments in the configurations and processing for acquiring an image of the affected-area region. In the description of this embodiment, identical configurations and processing to the first to third embodiments have been allocated identical reference symbols to those used in FIGS. 1 to 18, and a detailed description thereof has been omitted.

Figure 19:
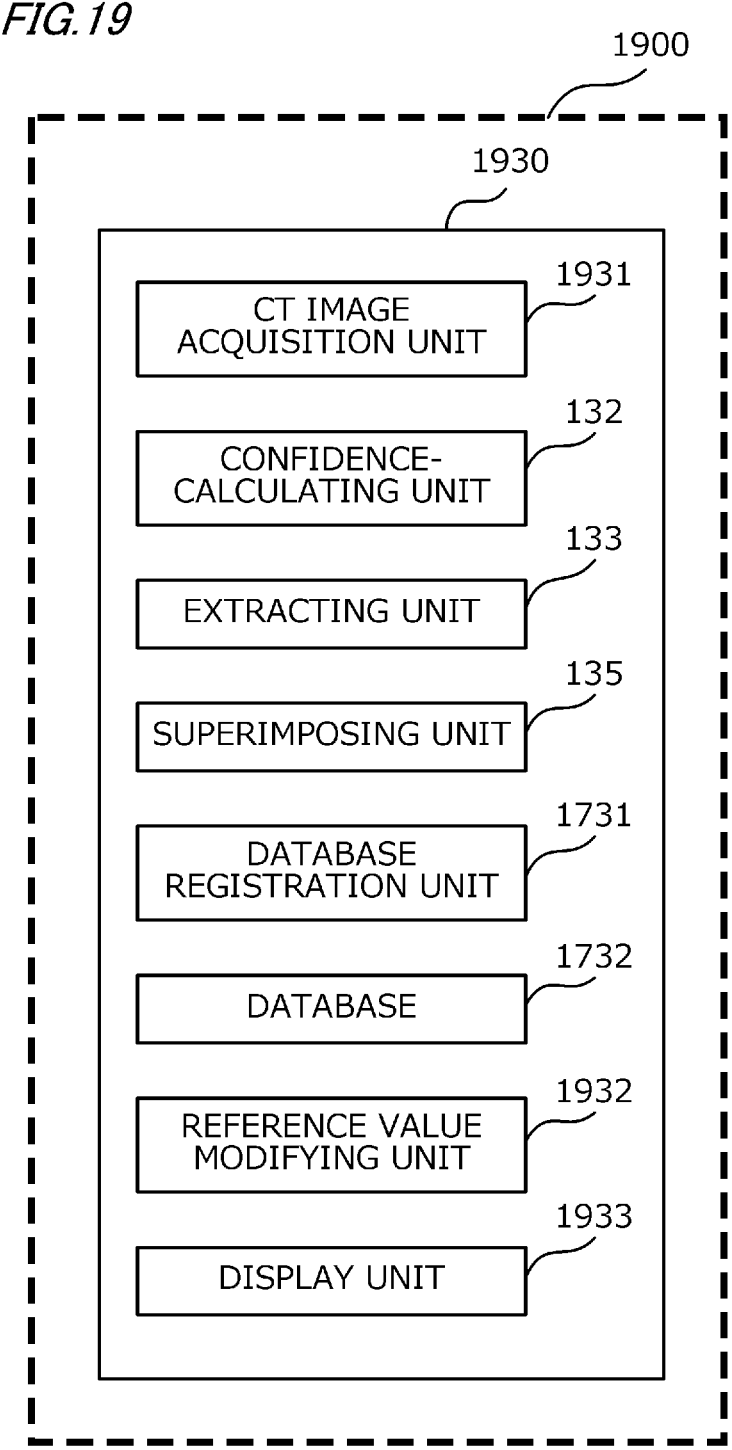
FIG. 19 is a view showing an example functional configuration of an image processing system of a fourth embodiment.

Functional Configuration and Hardware Configuration Referring to FIGS. 19 and 20, a functional configuration and a hardware configuration of an image processing system 1900 will be described. FIG. 19 is a view showing an example functional configuration of the image processing system according to the fourth embodiment.

The image processing system 1900 of this embodiment is constituted by an image processing apparatus 1930. The image processing apparatus 1930 includes a CT image acquisition unit 1931 in place of the imaging apparatus 120 of the first embodiment. Further, the image processing apparatus 1930, similarly to the image processing apparatus 130 of the first embodiment, includes the confidence-calculating unit 132, the extracting unit 133, and the superimposing unit 135. Furthermore, the image processing apparatus 1930, similarly to the image processing apparatus 1730 of the third embodiment, includes the database registration unit 1731 and the database 1732. The image processing apparatus 1930 also includes reference-value-modifying unit 1932 and display unit 1933 that are respectively similar to the reference-value-modifying unit 121 and the display unit 126 of the imaging apparatus 120.

The CT image acquisition unit 1931 acquires image data in a DICOM (Digital Imaging and COmmunication in Medicine) format, output from a CT scanner 2000 to be described below. DICOM is a standard defining a communication protocol and an image format for medical imaging equipment.

Similarly to the third embodiment, the database registration unit 1731 generates a record including the following information and registers the generated record in the database 1732 provided in the image processing apparatus 1730.

An image captured by the CT image acquisition unit 1931.

Information relating to the affected-area region 202 extracted by the extracting unit 133.

The confidence reference value modified by the reference-value-modifying unit 1932 (when the reference value is not modified, the confidence reference value used by the extracting unit 133 in SB504 and SB513).

Similarly to the third embodiment, the database 1732 is used to register records generated by the database registration unit 1731.

The reference-value-modifying unit 1932 modifies the confidence reference value used to extract the affected-area region 202 on the basis of a user operation.

The display unit 1933 performs various types of display control. The display unit 1933 displays the image acquired by the CT image acquisition unit 1931 on the output apparatus 440. Further, the display unit 1933 displays on the output apparatus 440 a display based on the information indicating the affected-area region 202 extracted by the extracting unit 133 and/or the information relating to the confidence reference value used by the extracting unit 133 to extract the affected-area region 202. Note that the display unit 1933 may display the information indicating the affected-area region 202 extracted by the extracting unit 133 and/or the information relating to the confidence reference value used by the extracting unit 133 to extract the affected-area region 202 so as to be superimposed on the image acquired by the CT image acquisition unit 1931.

Figure 20:
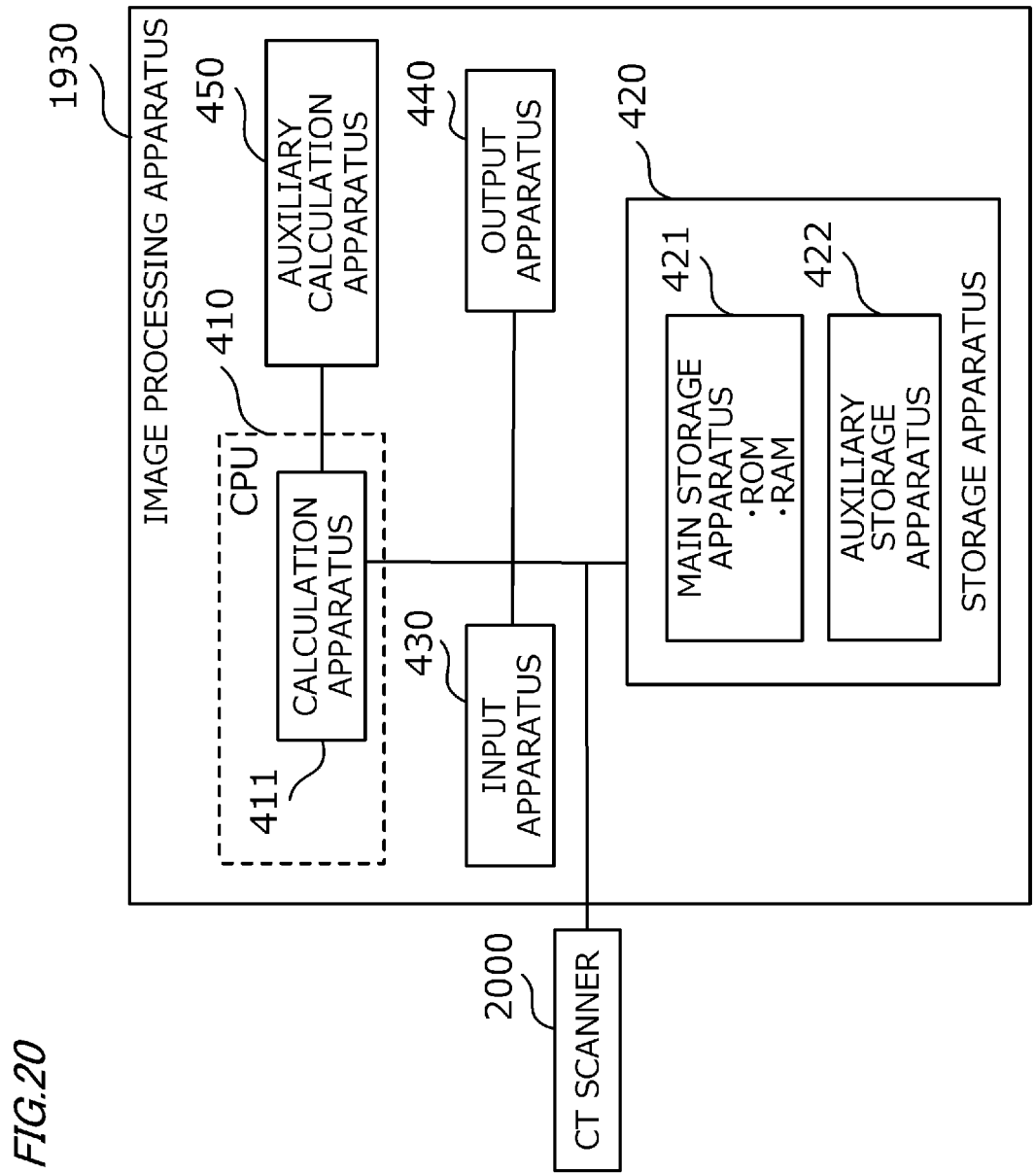
FIG. 20 is a view showing an example hardware configuration of an image processing apparatus of the fourth embodiment.

FIG. 20 is a view showing an example hardware configuration of the image processing apparatus according to the fourth embodiment. The image processing apparatus 1930 according to this embodiment is configured identically to the image processing apparatus 130 of the first embodiment and is also connected to the CT scanner 2000. The CT image acquisition unit 1931 of the image processing apparatus 1930 can acquire image data output from the CT scanner 2000.

The CT scanner 2000 is configured to acquire medical image data. The CT scanner 2000 may be replaced or supplemented by a scanner using a different medical imaging modality, such as an MRI scanner, an X-ray scanner, or a PET scanner, for example.

Operation of Image Processing System

Figure 21:
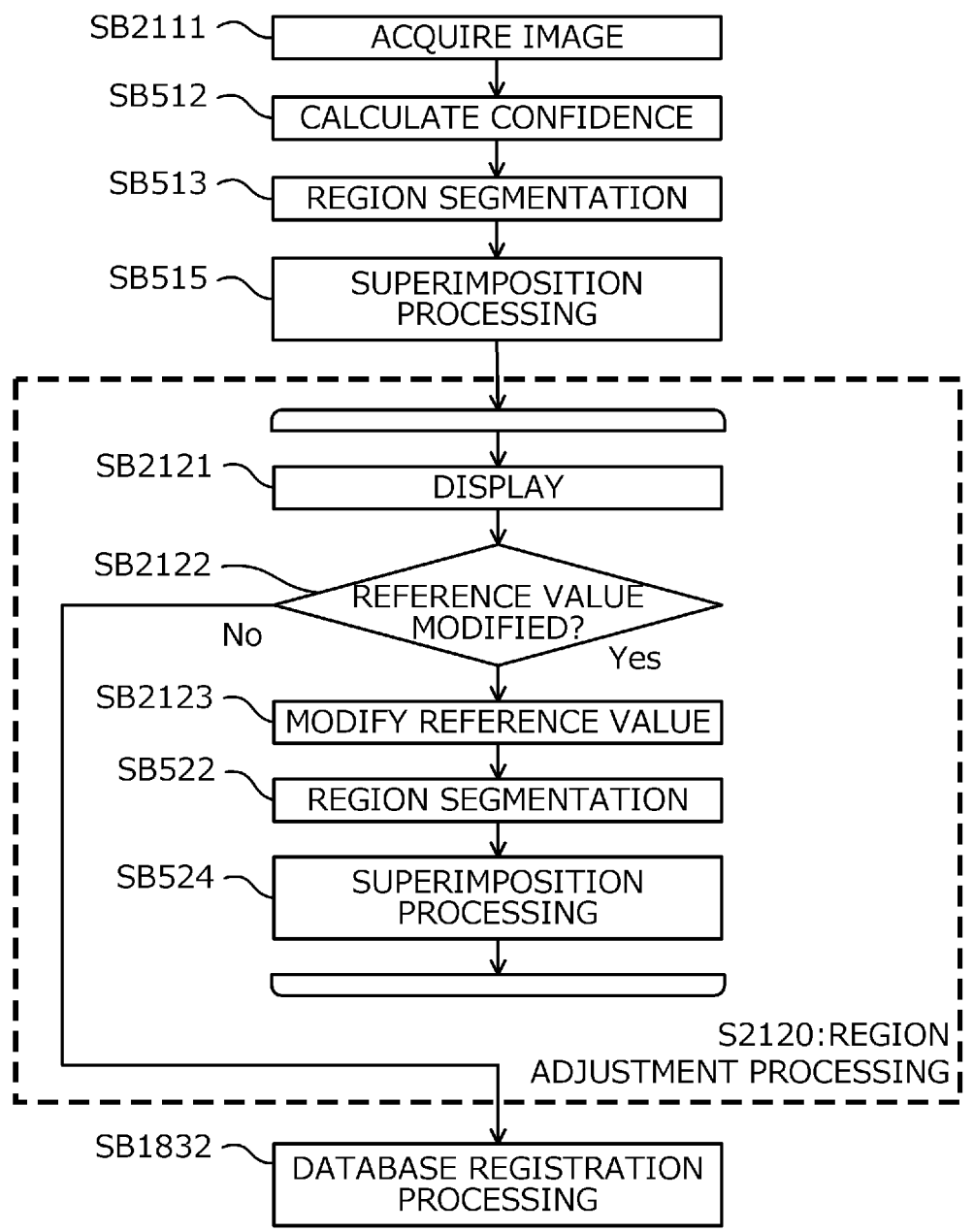
FIG. 21 is a view illustrating an example operation of the image processing system of the fourth embodiment.
Figure 22:
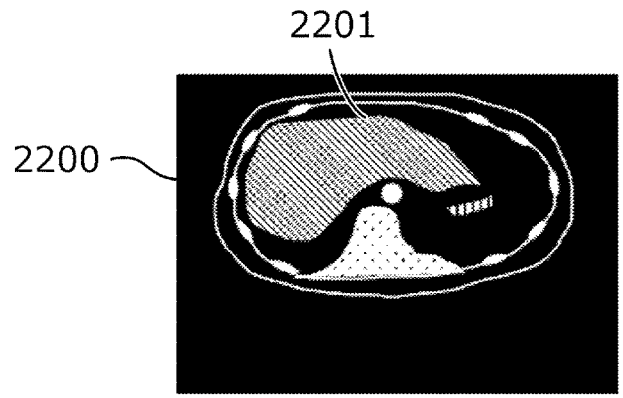
FIG. 22 is a view showing a second example of an image before superimposing the affected-area region.
Figure 23:
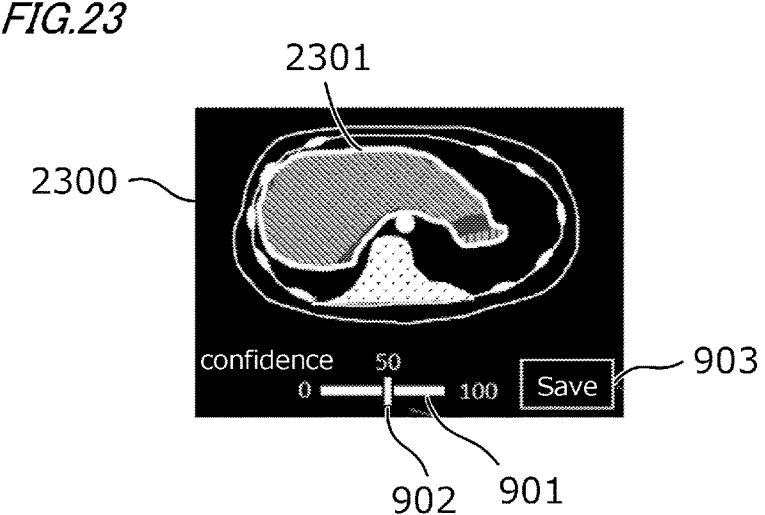
FIG. 23 is a view showing a fourth example of an image displaying the affected-area region before adjustment.
Figure 24:
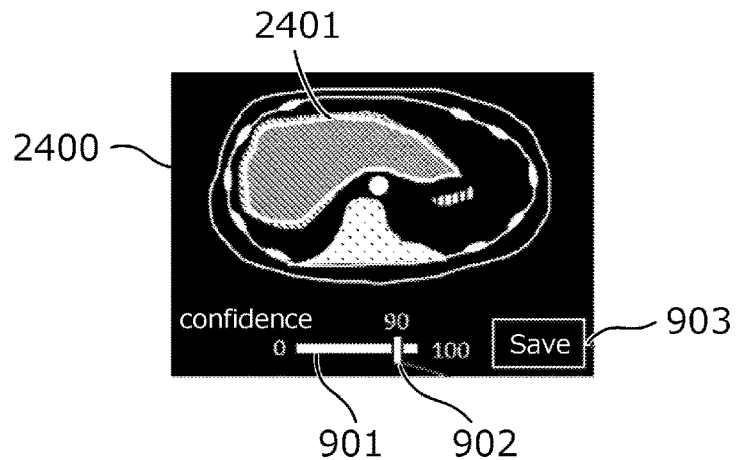
FIG. 24 is a view showing a fourth example of an image displaying the affected-area region after adjustment.

Referring to FIGS. 21 to 24, an operation of the image processing system according to this embodiment will be described. FIG. 21 is a view illustrating an example operation (an example of processing executed according to a flowchart) of the image processing system according to the fourth embodiment. FIG. 22 is a view showing a second example of an image before superimposing the affected-area region. FIGS. 23 and 24 are views showing fourth examples of images displaying the affected-area region before and after adjustment.

The processing executed by the image processing apparatus 1930 is realized by having the CPU 410 expand a program stored in the ROM of the main storage apparatus 421 in the system memory and execute the program. Note that the processing of FIG. 21 is started when power is supplied to the image processing apparatus 1930 and the image processing apparatus 1930 starts to acquire CT images from the CT scanner 2000.

In SB2111, the CT image acquisition unit 1931 acquires an image output from the CT scanner 2000. FIG. 22 shows an example of an image 2200 output from the CT scanner 2000. In this embodiment, the CT scanner 2000 scans the abdomen of the subject and outputs the image 2200 in DICOM format. A region 2201 of the image 2200 represents a cross section of the liver. In this embodiment, as shown in FIG. 23, the image processing apparatus 1930 extracts the liver region as an estimated area 2301 of the affected-area region, and makes fine adjustments to the extracted estimated area 2301 on the basis of user operations.

The image acquired by the CT image acquisition unit 1931 is not limited to the image data output from the CT scanner 2000. For example, the CT image acquisition unit 1931 may acquire image data from a remote data store (not shown) that can form a part of a PACS (Picture Archiving and Communication System). The CT image acquisition unit 1931 may also acquire an image stored in advance in the storage apparatus 420.

In SB512, similarly to the first embodiment, the confidence-calculating unit 132 calculates the confidence that each pixel of the image data depicts the liver on the basis of the image data acquired in SB2111. The details of the processing for calculating the confidence of each pixel are similar to those of the processing of SB503 and have, therefore, been omitted.

Next, in SB513, similarly to the first embodiment, the extracting unit 133 extracts, or performs region segmentation on, the estimated area 2301 from the image data acquired in SB2111 on the basis of the confidence of each pixel, calculated in SB512. The details of the processing for extracting or performing region segmentation on the estimated area 2301 are similar to those of the processing of SB504 and have, therefore, been omitted.

In SB515, similarly to the first embodiment, the superimposing unit 135 superimposes information indicating the estimated area 2301 extracted in FIG. 23, the button icon 903, and the slider 901 on the image 2200 from which the liver region 2201 was extracted. On an image 2300, the border of the extracted estimated area 2301 is denoted by a white line. The extracted estimated area 2301 is displayed in a superimposed fashion by a blending. The details of the superimposition processing are similar to those of the processing of SB506, described using FIGS. 7 and 8, and have, therefore, been omitted.

Referring to the image 2300 shown in FIG. 23 and an image 2400 shown in FIG. 24, an example of region adjustment processing S2120 shown in FIG. 21 will be described. The region adjustment processing S2120 is processing for adjusting the estimated area 2301 on the image 2300 displayed on the output apparatus 440 (the display unit 1933) of the image processing apparatus 1930 on the basis of a user operation. In the region adjustment processing S2120, as shown in FIG. 24, the estimated area 2301 of FIG. 23 is adjusted to an affected-area region 2401 that is close to the determination of the user.

In SB2121, the display unit 1933 displays the image 2300 subjected to superimposition processing in SB515 or the image 2300 subjected to superimposition processing in SB524 on the output apparatus 440. The estimated area 2301 before being adjusted by the user is displayed so as to be superimposed on the image 2300. The user can adjust the range of the affected-area region 2301 using the input apparatus 430.

In this embodiment, it is assumed that a mouse included in the input apparatus 430 is used as operating means for changing the display screen. By operating the mouse of the input apparatus 430, the user can adjust the estimated area 2301 (the region to be subjected to surface area measurement). Note that the operating means for adjusting the region is not limited to a mouse, and the touch panel display of the display apparatus 313 or a keyboard, or the like, included in the input apparatus 430 may be used instead.

In SB2122, similarly to SA522 of the first embodiment, the reference-value-modifying unit 1932 determines whether or not the reference value has been modified by a user operation in relation to the image 2300 displayed in SB2121. When the reference value has been modified, the processing advances to SB2123, and when the reference value has not been modified, the processing advances to SB1832. The details of the processing for adjusting the region by modifying the reference value are similar to those of the processing of SA522, described using FIGS. 9 and 10, and have, therefore, been omitted.

In SB2123, similarly to SA523 of the first embodiment, the reference-value-modifying unit 1932 modifies the reference value of the confidence as the liver in accordance with the position of the selecting member 902 of the slider 901, which was dragged by the user in SB2122. In FIG. 24, for example, the selecting member 902 of the slider 901 is moved by a user operation to a position of 90(%). Accordingly, the reference value of the confidence as the liver is modified to 90(%). In this case, by increasing the reference value, the affected-area region 2401 on the image 2400 is set in a smaller range than that of the estimated area 2301 shown in FIG. 23.

In SB522, similarly to the first embodiment, the extracting unit 133 extracts, or performs region segmentation on, the affected-area region 2401 from the image data acquired in SB2111 on the basis of the modified confidence reference value. The extracting unit 133 can extract, or perform region segmentation on, the affected-area region 2401 on the basis of the confidence calculated for each pixel in SB512 and the information relating to the confidence reference value modified in SB2123. The details of the extraction or region segmentation processing are similar to the first embodiment and have, therefore, been omitted.

In SB524, similarly to SB515, the superimposing unit 135 superimposes the information indicating the adjusted affected-area region 2401, the button icon 903, and the slider 901 on the image data used to extract the estimated area 2301. The details of the superimposition processing are similar to those of the processing of SB506 and SB515, described using FIGS. 7 and 8, and have, therefore, been omitted.

Note, however, that, in SB524, as indicated by the image 2400 shown in FIG. 24, the superimposing unit 135 performs superimposition after modifying the position of the selecting member 902 of the slider 901 to a position corresponding to the value of the reference value modified in SB2123. FIG. 24 shows a case in which the confidence reference value is modified from 50(%) to 90(%) in SB2123.

In SB1832, similarly to the third embodiment, the database registration unit 1731 generates a record including the following information and registers the generated record in the database 1732 provided in the image processing apparatus 1930.

The CT image 2200 acquired in SB2111.
The affected-area region 2401 finally extracted by the extracting unit 133 in SB513 or SB522.
The confidence reference value modified by the reference-value-modifying unit 1932 in SB2123 (when SB2123 is not executed so that the reference value is not modified, the confidence reference value used by the extracting unit 133 in SB513).

Actions and Effects of Fourth Embodiment According to this embodiment, as described above, the image processing apparatus 1930 modifies the reference value of the confidence as the liver on the basis of a user operation. The image processing apparatus 1930 analyzes an image acquired from the CT scanner 2000 and extracts a set of pixels exceeding the confidence reference value modified by the user as the adjusted affected-area region 2401. The display unit 1933 of the image processing apparatus 1930 displays the affected-area region 2401 extracted in accordance with the confidence reference value modified by the user in a superimposed fashion on the output apparatus 440. The user (a healthcare worker such as a doctor), when performing a liver transplant, for example, can check whether or not the liver region has been extracted appropriately from a CT image of the abdomen of the liver provider (donor). When a region that differs from the determination of the user is extracted, the user can modify the confidence reference value of the determination as the liver region. The user can make fine adjustments interactively while visually confirming changes to the extracted affected-area region. The image is not limited to a CT image of the abdomen, and the user may input an image of the affected area of a different case into the image processing apparatus 1930. Thus, the user can make fine adjustments to the extracted affected-area region interactively in a similar manner in relation to an affected-area region of a different case.

Note that the embodiments described above merely illustrate specific examples of embodiments of the present invention, and the technical scope of the present invention is not to be interpreted as being limited thereby. In other words, the present invention may be embodied in various forms without departing from the technical spirit or the principle features thereof.

For example, the above embodiments cite examples of application to the assessment of an affected-area region in which a pressure ulcer has developed, but the present invention is not limited to a pressure ulcer and may also be applied to the measurement and assessment of an affected-area region of a burn, a laceration, or the like, another medically affected-area region, and so on. For example, the present invention may also be applied to measurement and assessment by an X-ray CT (Computer Tomography) apparatus or an MRI (Magnetic Resonance Imaging) apparatus. The present invention may also be applied to a case in which a region of an organ such as the liver is measured from a two-dimensional tomographic image or a three-dimensional image acquired and reconstructed by a medical image diagnosis apparatus such as a PET (Positron Emission Tomography) apparatus. With regard to the liver, for example, the present invention can be applied to a case in which a liver region is estimated from a CT image in order to confirm, during a liver transplant, whether or not the liver of the provider (the donor) is of an appropriate size for the recipient patient.

Note that the various types of control described above as being performed by the system control circuit 310 of the imaging apparatus or the CPU 410 of the image processing apparatus may each be performed by a single piece of hardware. Further, regarding the various types of control described above, the control of the imaging apparatus, the image processing apparatus, or the image processing system may be performed by apportioning the processing among a plurality of pieces of hardware. Furthermore, the present invention was described in detail on the basis of preferred embodiments thereof, but the present invention is not limited to these specific embodiments and includes various embodiments within a scope that does not depart from the spirit of the invention. Moreover, the embodiments described above merely illustrate one embodiment of the present invention, and the embodiments may be combined as appropriate.

Furthermore, in the above embodiments, cases in which the present invention is applied to an imaging apparatus and an image processing apparatus were described as examples, but the present invention is not limited to these examples and may be applied to any image processing apparatus capable of displaying captured images. More specifically, the present invention can be applied to a personal computer, a PDA, a portable telephone terminal, a portable image viewer, or a printer apparatus that includes a display. The present invention can also be applied to a digital photo frame, a music player, a game machine, an electronic book reader, a tablet terminal, a smartphone, a projection apparatus, a household appliance or in-vehicle apparatus that includes a display, and so on.

According to the present invention, a user can adjust a region of interest extracted from an image of a subject while visually checking the region of interest.

OTHER EMBODIMENTS

Embodiment(s) of the present invention can also be realized by a computer of a system or an apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., an application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™) a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
one or more processors and a memory storing instruction that, when executed by the one or more processors, cause the image processing apparatus to function as:
an acquisition unit configured to acquire image data;
a calculation unit configured to calculate, for each unit region of the image data, a confidence that the unit region is an extraction subject, the confidence as the extraction subject being calculated for each unit region of the image data by inputting the image data into a trained model of a neural network that has been trained using images of an existing extraction subject or a region of interest as training data;
a modification unit configured to modify a reference value of the confidence, which is used to extract a region of interest;
an extraction unit configured to extract the region of interest on the basis of the calculated confidence of each unit region and the modified reference value;
a display unit configured to display the extracted region of interest; and
an assessment unit configured to calculate a surface area of the region of interest on the basis of inclination and variation in a depth direction of the subject, which are detected from the image data.

2. The image processing apparatus according to claim 1, wherein the modification unit modifies the reference value of the confidence on the basis of a user operation.

3. The image processing apparatus according to claim 1, wherein the modification unit modifies the reference value of the confidence on the basis of a user operation on a GUI (Graphical User Interface).

4. The image processing apparatus according to claim 1, wherein the modification unit modifies the reference value of the confidence on the basis of the confidence relating to a unit region selected by the user.

5. The image processing apparatus according to claim 1, wherein the extraction unit extracts, as the region of interest, a set of unit regions in which values of the calculated confidence of the unit regions equal or exceed the modified reference value of the confidence.

6. The image processing apparatus according to claim 1, wherein the calculation unit calculates, for each unit region of the image data, a confidence as the extraction subject and a confidence as another extraction subject, the modification unit modifies at least one of a reference value of the confidence as the extraction subject and a reference value of the confidence as the other extraction subject, and the extraction unit extracts the region of interest on the basis of the confidence as the extraction subject, the confidence as the other extraction subject, and the modified reference value.

7. The image processing apparatus according to claim 1, wherein the extraction unit re-extracts a partial region that partially overlaps the region of interest on the basis of the confidence relating to a unit region selected by the user.

8. The image processing apparatus according to claim 7, wherein the partial region is a region including the unit region selected by the user.

9. The image processing apparatus according to claim 7, wherein the extraction unit re-extracts a region outside the partial region on the basis of the reference value prior to the re-extraction.

10. The image processing apparatus according to claim 1, wherein, when the region of interest is divided into a plurality of regions, the extraction unit re-extracts a partial region that overlaps at least any of the plurality of regions on the basis of the confidence relating to a unit region selected by the user.

11. The image processing apparatus according to claim 1, further comprising a storage unit configured to store information relating to a region of interest that is re-extracted on the basis of the modified reference value by the extraction unit when the reference value of the confidence has been modified by the modification unit,
wherein the calculation unit modifies the reference value of the confidence on the basis of the stored information relating to the region of interest.

12. The image processing apparatus according to claim 11, wherein, when the reference value of the confidence is modified, the storage unit stores the modified reference value, and the extraction unit extracts the region of interest on the basis of the stored reference value of the confidence.

13. The image processing apparatus according to claim 1, wherein the image data include an affected-area region, and, when the reference value of the confidence is increased, the extraction unit extracts, as the region of interest, a more central region of the affected-area region than before the reference value of the confidence is increased.

14. A control method of controlling an image processing apparatus, the method comprising:
an acquisition step of acquiring image data;
a calculation step of calculating, for each unit region of the image data, a confidence that the unit region is an extraction subject, the confidence as the extraction subject being calculated for each unit region of the image data by inputting the image data into a trained model of a neural network that has been trained using images of an existing extraction subject or a region of interest as training data;
a modification step of modifying a reference value of the confidence, which is used to extract the region of interest;
an extraction step of extracting the region of interest on the basis of the calculated confidence of each unit region and the modified reference value;
a display step of displaying the extracted region of interest; and
an assessment step of calculating a surface area of the region of interest on the basis of inclination and variation in a depth direction of the subject, which are detected from the image data.

15. A non-transitory computer readable medium that stores a program, wherein the program causes a computer to execute:
an acquisition step of acquiring image data;
a calculation step of calculating, for each unit region of the image data, a confidence that the unit region is an extraction subject, the confidence as the extraction subject being calculated for each unit region of the image data by inputting the image data into a trained model of a neural network that has been trained using images of an existing extraction subject or a region of interest as training data;
a modification step of modifying a reference value of the confidence, which is used to extract the region of interest;
an extraction step of extracting the region of interest on the basis of the calculated confidence of each unit region and the modified reference value;
a display step of displaying the extracted region of interest; and
an assessment step of calculating a surface area of the region of interest on the basis of inclination and variation in a depth direction of the subject, which are detected from the image data.

* * * * *